US008655441B2

(12) United States Patent
Fletcher et al.

(10) Patent No.: US 8,655,441 B2
(45) Date of Patent: Feb. 18, 2014

(54) METHODS AND APPARATUS FOR MONITORING PATIENTS AND DELIVERING THERAPEUTIC STIMULI

(75) Inventors: Richard Fletcher, Medford, MA (US); Rosalind Picard, Newton, MA (US); Hoda Eydgahi, Salisbury, MD (US); Clayton Williams, Heber City, UT (US)

(73) Assignee: Massachusetts Institute of Technology, Cambridge, MA (US)

(*) Notice: Subject to any disclaimer, the term of this patent is extended or adjusted under 35 U.S.C. 154(b) by 555 days.

(21) Appl. No.: 12/834,903

(22) Filed: Jul. 13, 2010

(65) Prior Publication Data

US 2011/0004072 A1    Jan. 6, 2011

Related U.S. Application Data

(63) Continuation-in-part of application No. 12/386,348, filed on Apr. 16, 2009, now Pat. No. 8,140,143.

(51) Int. Cl.
*A61B 5/0482* (2006.01)
*A61B 5/04* (2006.01)
*A61B 5/0404* (2006.01)
*A61B 5/021* (2006.01)

(52) U.S. Cl.
USPC ............ 600/545; 600/382; 600/386; 600/508

(58) Field of Classification Search
USPC .................. 600/372, 382, 384, 386, 388–393, 600/508–509, 544–547
See application file for complete search history.

(56) References Cited

U.S. PATENT DOCUMENTS

| 2,829,638 | A | 4/1958 | Douglas |
| 3,870,034 | A | 3/1975 | James |
| 6,415,176 | B1 | 7/2002 | Scheirer et al. |
| 6,599,243 | B2 * | 7/2003 | Woltermann et al. ......... 600/300 |
| 2002/0032386 | A1 | 3/2002 | Sackner et al. |
| 2002/0038092 | A1 | 3/2002 | Stanaland et al. |
| 2002/0198574 | A1 | 12/2002 | Gumpert |

(Continued)

FOREIGN PATENT DOCUMENTS

| EP | 1886707 A1 | 2/2008 |
| WO | 2009023937 A1 | 2/2009 |

OTHER PUBLICATIONS

R. Picard, C. Du, Monitoring Stress and Heart Health with a Phone and Wearable Computer, Motorola Offspring Journal, vol. 1, Nov. 2002.

(Continued)

*Primary Examiner* — Linda Dvorak
*Assistant Examiner* — Brian M Antiskay
(74) *Attorney, Agent, or Firm* — Stephen R. Otis

(57) ABSTRACT

In an exemplary implementation of this invention, a user wears comfortable biosensors. These sensors gather physiological data from the user and transmit this data to another radio-enabled device. This other device may be a mobile phone. The data is further transmitted, via this other radio-enabled device, to one or more networks (such as wireless networks or the Internet). A processor analyzes this transmitted data, in real time, to recognize patterns in the data that indicate the need for therapeutic intervention. Upon recognition of such a pattern, the processor outputs instructions for a transducer to deliver therapeutic stimuli. These instructions are transmitted, over one or more wired or wireless networks, to a transducer which delivers the therapeutic stimuli to the user.

20 Claims, 18 Drawing Sheets

(56) References Cited

U.S. PATENT DOCUMENTS

| | | |
|---|---|---|
| 2003/0004424 A1 | 1/2003 | Birnbaum |
| 2003/0117651 A1 | 6/2003 | Mastraszek |
| 2004/0073121 A1 | 4/2004 | Sun |
| 2005/0107655 A1 | 5/2005 | Holzner |
| 2006/0069319 A1 | 3/2006 | Elhag et al. |
| 2006/0211934 A1 | 9/2006 | Hassonjee et al. |
| 2006/0293608 A1 | 12/2006 | Rothman et al. |
| 2008/0167535 A1 | 7/2008 | Stivoric et al. |
| 2008/0214089 A1 | 9/2008 | Vermac et al. |
| 2009/0326406 A1* | 12/2009 | Tan et al. ............ 600/546 |

OTHER PUBLICATIONS

D. Gustafson, T. Palesh, R. Picard, P. Plsek, L. Maher, V. Capoccia, "Automating Addiction Treatment: Enhancing the Human Experience and Creating a Fix for the Future", Future of Intelligent and Extelligent Health Environment, R. Bushko, editor, pp. 186-206, IOS Press, 2005.

H. Eydgahi, Design and Evaluation of iCalm: A Novel, Wrist-Worn, Low-Power, Low-Cost, Wireless Physiological Sensor Module, Masters Thesis, Massachusetts Institute of Technology, published Dec. 22, 2008.

M. Morris, F. Guilak, Mobile Heart Health: Project Highlight, IEEE Pervasive Computing, vol. 8 Issue 2, pp. 57-61, Apr. 17, 2009.

International Search Report and Written Opinion of the International Searching Authority, Jul. 20, 2010, PCT/US2010/031115.

Nonfinal Office Action, mailed Jun. 22, 2011, USPTO, U.S. Appl. No. 12/386,348.

M. Strauss et al., "The HandWave Bluetooth Skin Conductance Sensor", J. Tao, T. Tan, R. Picard, editors, ACII, vol. 3784 of Lectures Notes in Computer Science, pp. 699-706, Springer, 2005.

T. Westeyn et al., ActionGSR: A Combination Galvanic Skin Response-Accelerometer for Physiological Measurements in Active Environnments, iscw, pp. 129-130, 2006 10th IEEE International Symposium on Wearable Computers, 2006.

R. Picard, et al. The Galvacticator: A Glove that Senses and Communicates Skin Conductivity, Proc. of 9th International Conference on Human-Computer Interaction, pp. 1538-1542 (2001).

* cited by examiner

Resistance values are in units of Ohms

Resistance values are in units of Ohms

METHODS AND APPARATUS FOR MONITORING PATIENTS AND DELIVERING THERAPEUTIC STIMULI

RELATED INVENTION

This application is a continuation-in-part of U.S. non-provisional patent application Ser. No. 12/386,348 filed on Apr. 16, 2009, the entire disclosure of which is incorporated by reference herein.

FIELD OF THE TECHNOLOGY

The present invention relates generally to wireless biosensors.

SUMMARY

It is an object of this invention to remotely monitor physiological parameters of a patient, and—in real time—to analyze data gathered by this monitoring to recognize patterns that indicate the need for intervention, and then—also in real time—to deliver therapeutic stimuli to the patient via a transducer in a handheld or wearable device.

There are many situations where therapeutic stimuli can be used to help a person mitigate or prevent undesirable health events or unhealthy behaviors. Such stimuli are often described in the broader sense as "therapeutic interventions." The present invention may be implemented with a network architecture that enables automatic detection of an undesirable state and enables a corresponding appropriate health intervention to be delivered in real-time.

As one example, consider a person with Autism Spectrum Disorder (ASD) that may experience episodes of extreme stress or panic attacks, better-known as "meltdowns." Such episodes are associated with a high degree of electrodermal activity (EDA), otherwise known as skin conductance or "galvanic skin response." It has been demonstrated that the use of touch, weighted blankets or other haptic stimuli can be used to provide calming comfort in these situations and reduce recovery time. [Champagne, T., and Mullen, B. (2005) The Weighted Blanket: Use and Research in Psychiatry. MAOT 2005] According to principles of this invention, this meltdown state can be automatically detected through the use of wearable physiological sensors to detect electrodermal activity, and a therapeutic stimulus can be automatically applied through the use of wearable transducers.

In another example, consider a veteran suffering from post-traumatic stress disorder ("PTSD"). The onset of a PTSD "dream episode" causes a pattern of physiological changes in the veteran. In an illustrative implementation of this invention, this pattern is recognized in real time. A wristband worn by the veteran delivers, in real time, a vibration or sound to the veteran. This therapeutic stimulus (vibration or sound) may trigger a startle response that helps the veteran "snap out" of the episode and re-engage with reality.

Also, consider the problem of apnea in very young infants. At this stage of development, the central nervous system is not always fully developed and some infants will temporarily stop breathing (apnea), which can lead to death if breathing is not restored. This invention may be implemented in such a way that one or more physiological sensors are used to detected signs of apnea (reduction in breathing, change in heart rate, and decrease in blood oxygen saturation). These signs can be recognized in real time and a foot vibrator activated to trigger the infant to resume breathing.

Or, for example, consider a patient who has become addicted to a "prescription opioid" such as morphine, codeine, oxycodone, hydrocodone, hydromorphone, or Tramadol® (a synthetic analog of codeine), and is experiencing the onset of a drug craving. Changes in the patient's physiological parameters indicate the start of this craving. In an illustrative implementation of this invention, these changes may be recognized in real time. A message may be sent in real time to the patient's cell phone, with a picture of the patient's daughter and a message that says "Dad, you promised not to take morphine again. I love you". These therapeutic stimuli (the picture and message), delivered in this timely way, may help the patient resist the drug craving.

In some applications, the detection or classification of a particular physiological state or condition can be implemented by monitoring a single physiological parameter (e.g. electrodermal activity) and using a simple threshold function. However, in most cases which involve multiple sensor inputs and multiple degrees of freedom, it is necessary to use one or more processors that can analyze the physiological data using a real-time machine learning algorithm that can implement state classification in a high multidimensional space.

In an exemplary implementation of this invention, the patient wears a wearable washable biosensor, such as that described in United States non-provisional patent application Ser. No. 12/386,348 filed on Apr. 16, 2009.

This invention may be implemented using different kinds of physiological data. For example, data regarding heart beat, breathing, skin conductance, biopotentials, body core temperature, optical reflectance of blood vessels or limb movement may be monitored.

In exemplary implementations of this invention, a patient (e.g. an infant) wears a battery-powered, comfortable biosensor for real-time, remote monitoring of physiological parameters such as electro-dermal activity (EDA), heart rate, and blood oxygen saturation. The biosensor wirelessly transmits this data using the IEEE 802.15.4 protocol, which is well-suited for low-power, low-duty cycle transmission. In proximity to the patient is a small data hub that acts as a bridge between IEEE 802.15.4 and Bluetooth™ signals. The data hub transmits the data using a Bluetooth™ radio to a Bluetooth™-enabled device (such as a smartphone, computer or radio base station) for further transmission over a second wireless network or the Internet. A remote processor analyzes this transmitted physiological data to identify states that require intervention. For example, the processor may recognize, in real time, a pattern in the data that indicates the onset of apnea in a premature infant. The processor outputs instructions for delivering therapeutic stimuli to a patient, in real time, via at least one transducer that is also worn by the patient.

Alternately, this invention may be implemented so that Bluetooth™ is incorporated directly in the wearable sensor, thus allowing the sensors to communicate directly to the mobile phone. In this approach, the sensor can perform some basic filtering of the sensor data and only wirelessly connect to the mobile phone periodically (two times per second) in order to save power. The phone acts as the wireless "hub" to relay data to an external server using the external cell phone data network or via SMS or MMS messaging. This approach is advantageous in some contexts in which a patient is ambulatory.

According to principles of this invention, a transducer used to deliver therapeutic stimuli may be wearable, such as a small vibrating motor. Alternately, the transducers used to deliver therapeutic stimuli may be housed in a handheld device, such as a mobile phone. For example, a remote server can send an MMS message to the patient via a mobile phone, in the form of an image or audio file that has a psychological impact on the patient.

In some embodiments of this invention, the processor may engage in machine learning to improve pattern recognition. This machine learning may be used to customize pattern identification for a specific patient or specific medical condition. The machine learning may employ one or more methods. However, the exemplary implementation makes use of Dynamic Bayesian Networks, which is particularly suited for analyzing temporal characteristics in high-dimensional parameter spaces.

This invention may be implemented in such a way that it can handle multiple patients at the same time. In such an embodiment, the remote processor analyzes data gathered from multiple patients and multiple hub devices. When the processor recognizes a state that requires immediate intervention, therapeutic stimuli are delivered to the corresponding patient in real time.

This invention may be implemented in such a way as to function as a "reverse hotline". In this implementation, upon recognition of a pattern requiring intervention, the system notifies one or more humans, and facilitates the delivery of a live message from at least one person directly to the patient. This live human social input delivered in real time may have a powerful therapeutic effect.

Here are some ways that this invention may be implemented:

This invention may be implemented as a system comprising, in combination: (a) at least one sensor for measuring physiological data, (b) at least one hub adapted for receiving wireless signals that are communications directly or indirectly from said sensor and for transmitting wireless signals that are communications to a network, wherein said received signals comply with a wireless protocol that is not identical to the wireless protocol with which said transmitted signals comply, and (c) one or more processors for recognizing at least one pattern in said physiological data, and based upon said recognition, for outputting instructions for at least one transducer to produce therapeutic stimuli. Furthermore: (1) at least some of said transmitted signals or said received signals may comply with a Bluetooth™ wireless protocol, (2) at least one said processor may be adapted for analyzing data transmitted by a plurality of hubs, (3) said pattern may be indicative of a drug craving or panic state, (4) said therapeutic stimuli may comprise a verbal message, (5) said therapeutic stimuli may comprise haptic or thermal stimuli, (6) at least one said sensor may be wearable, (7) said system may further comprise at least one said transducer, (8) at least one said transducer may be housed or carried in a wearable device, (9) at least one of said processors may be further adapted for machine learning that uses at least part of said physiological data as training data, (10) said system may be adapted to repeatedly: (I) accept updated physiological data, (II) use at least some of said updated physiological data as training data for machine learning, (III) based on said machine learning, revise at least one pattern recognition algorithm, and (IV) use said revised pattern recognition algorithm in a processor housed onboard a wearable or handheld device, (11) one or more of said processors may be further adapted for analyzing said physiological data regarding a user, accessing audio or visual content stored in machine-readable form in memory, and outputting instructions for at least one said transducer to deliver said content to said user in a form perceptible to said user, (12) said system may be adapted for performing said pattern recognition in real time, and (13) said system may be further adapted for soliciting at least one live human communication and outputting instructions for said communication to be delivered to a person wearing said at least one sensor.

This invention may be implemented as a system comprising, in combination: (a) at least one sensor for measuring physiological data regarding a user, and (b) one or more processors for recognizing at least one pattern in said physiological data, and based upon said recognition, for outputting instructions for obtaining at least one live human communication and causing it to be delivered to said user in a form perceptible by said user. Furthermore, said pattern recognition and output of instructions may occur in real time relative to at least one said pattern.

This invention may be implemented as a method comprising the following steps, in combination: (a) the receipt by a hub of wireless signals directly or indirectly from a sensor, (b) the transmission by said hub of wireless signals, wherein said received signals comply with a wireless protocol that is not identical to the wireless protocol with which said transmitted signals comply, and (c) the processing of said transmitted signals in such a way as to recognize at least one pattern in physiological data measured by said sensor, and based on said recognition, to output instructions for at least one transducer to deliver therapeutic stimuli to said user, wherein said pattern recognition occurs in real time. This method may further comprise the step of performing machine learning that uses at least part of said physiological data as training data.

DETAILED DESCRIPTION

Figure 1:
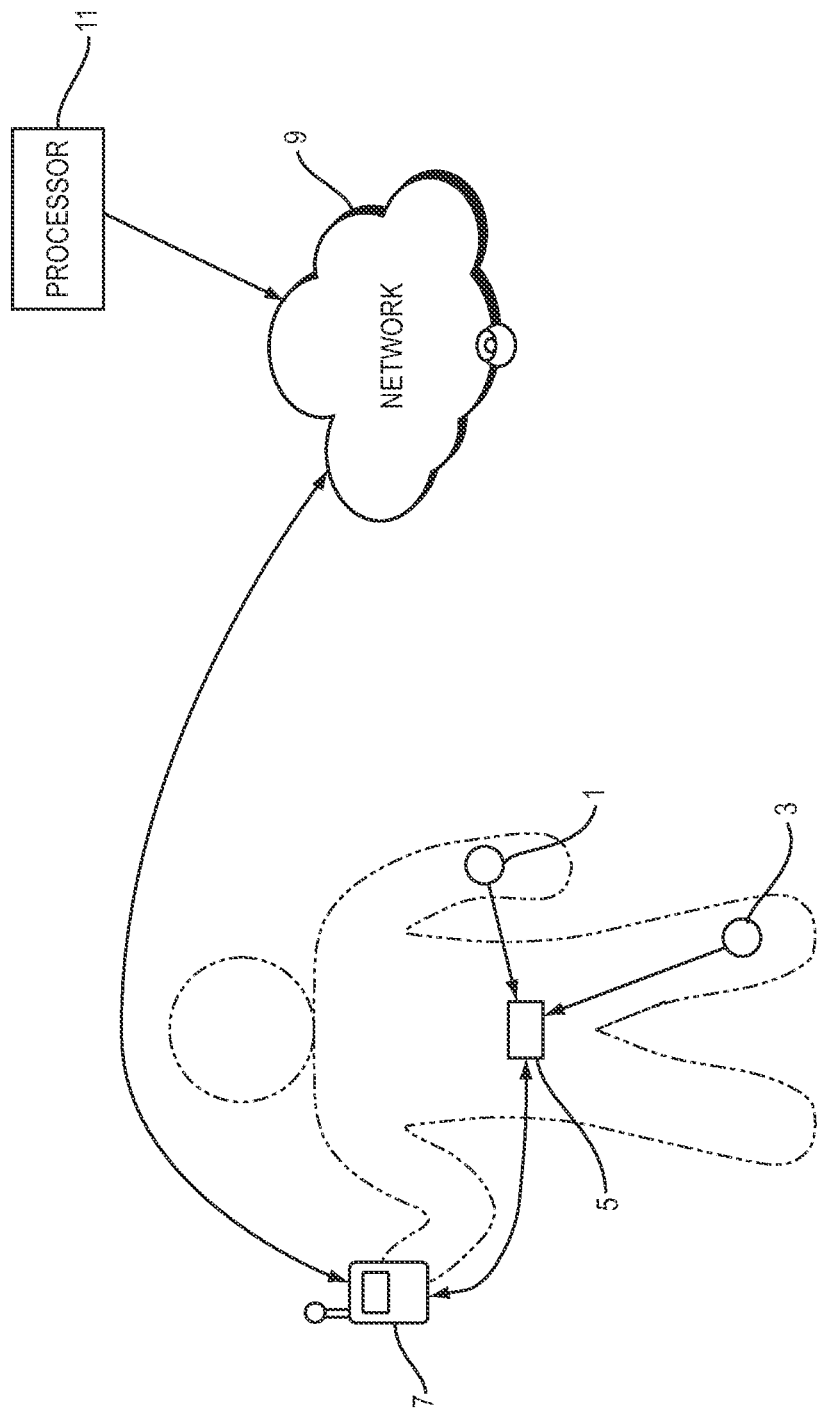
FIG. 1 is a diagram of a system for remotely monitoring physiological data and delivering therapeutic stimuli in real time, in an illustrative implementation of this invention.

FIG. 1 is a diagram that shows, at a high level, the functionality of an exemplary implementation of this invention. A user wears battery-powered, comfortable biosensors 1, 3 for measuring electro-dermal activity (EDA) and pulse rate. These biosensors wirelessly transmit this physiological data (EDA and pulse rate) using the IEEE 802.15.4 protocol. The IEEE 802.15.4 protocol allows low-power transmission, which is desirable in order to reduce the power drain on battery-operated sensors. The transmitted data is received by a small data hub 5 worn by the user. The wearable data hub 5 acts as a Bluetooth™ gateway, transmitting the data using a Bluetooth™ protocol. A Bluetooth™-enabled mobile phone 7 receives this data, and then wirelessly transmits it using at least one wireless network 9.

A processor 11 in a remotely located computer analyzes this physiologic data in real time, after it has been transmitted over the wireless network 9. The processor 11 uses pattern detection algorithms to detect patterns in this data that indicate that therapeutic intervention is appropriate. For example, a processor 11 may detect a pattern that indicates that the user is experiencing the onset of a drug craving, or the onset of a PTSD "dream" episode, or the onset of an autistic meltdown episode, or a panic state.

Upon detecting such a pattern, the processor 11 outputs instructions for delivering therapeutic stimuli to the user via at least one transducer in a handheld or mobile device. These instructions may be wirelessly transmitted over a wireless network 9 to a mobile phone 7. Pursuant to these instructions, transducers in the mobile phone 7 may display an audio or visual message such as a text message that comprises the therapeutic stimuli. For example, if the processor 11 has detected the onset of a drug craving, the cell phone may display an inquiry "how strong are you feeling right now?" and then a picture of the patient's daughter and a text message that says "Dad, you promised not to take morphine again. I love you".

This invention may be implemented so that a processor selects one out of several pre-recorded messages for a transducer to display. The message that is displayed may first ask the person how he/she is doing and then display encouragement or other support, e.g. a reminder of cognitive-behavior therapy, depending on the pattern detected and the patient's response to this inquiry.

Alternately, pattern analysis and other processing may be divided up, so that some is done onboard a sensor, and some is done offboard.

In the example shown in FIG. 1, a wireless hub 5 collects, aggregates, and stores data from the wireless sensors without the need for any reader infrastructure. The wireless hub can then relay this data to a remote network via a Bluetooth™ connection and a user's mobile phone. Alternatively, the system can be operated in a store—and forward manner by keeping the data stored on the wearable data hub until the user comes within range of an external reader device and then transmitting the data out to the network.

A wireless hub 5 that "bridges" a Bluetooth™ network and a IEEE 802.15.4 network has at least four advantages, in exemplary embodiments of this invention. First, it allows long battery life and small size/weight for the sensors. Second, it allows integration with Bluetooth™-enabled mobile devices. Third, a wireless hub provides the function of local data storage, which allows the system to be operated without any mobile phone at all. Fourth, integration with mobile phones (over Bluetooth™) allows information to be both sent and received via a cell phone network and Internet. Thus for data-logging or experience sampling applications, the physiological data can be wirelessly transmitted and logged on a remote internet server. However, without a cell phone, the data can be logged on the internal memory of the wireless hub.

Figure 2:
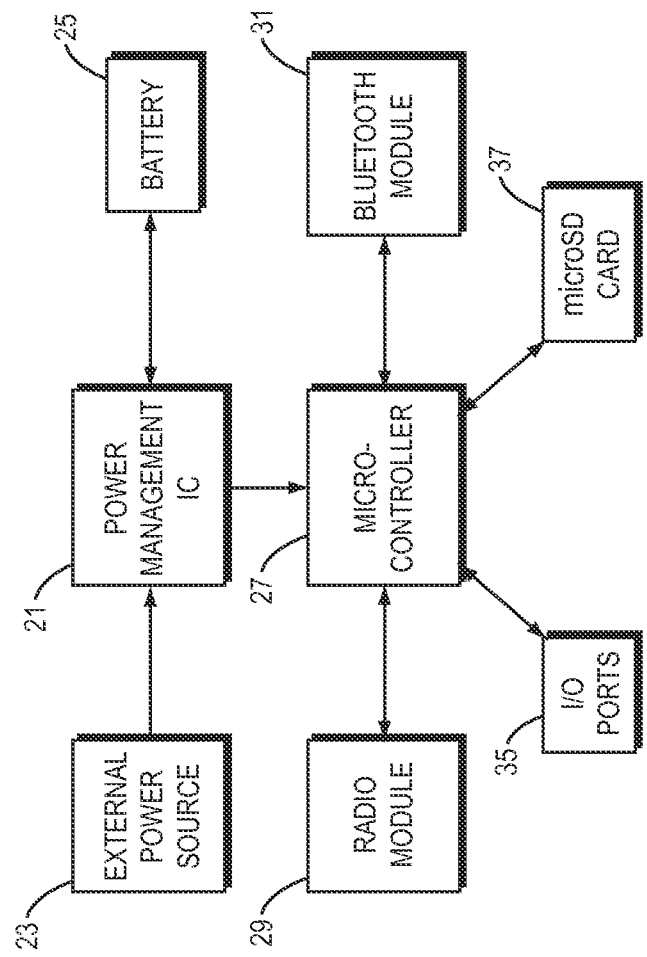
FIG. 2 is a diagram of a wearable data hub used as a Bluetooth™ gateway, in an illustrative implementation of this invention.

FIG. 2 is a block diagram of a wearable data hub that acts as a bridge between IEEE 802.15.4 and Bluetooth™ signals, in an illustrative implementation of this invention.

In the example shown in FIG. 2, a power management IC (integrated circuit) 21 controls the power supplied to the entire board of the hub. For example, this IC may be an LTC3557 (available from Linear Technology Corporation, Milpitas, Calif.). This IC takes a +5V DC input, and supplies the rest of the board with +3.3V. The 5+V input may come from a rechargeable Li-ion battery 25 or from an external power source 23 (such as an AC adaptor or USB cable). In a context where the hub is being worn by a user who is moving around, a battery may supply the power.

In FIG. 2, an Atmel® AVR® microcontroller 27 acts as a central manager for devices mounted on the hub. For example, this microcontroller may be an ATmega644P or ATmega644PA (available from Atmel Corporation, San Jose, Calif.). The microcontroller 27 is connected to the IEEE 802.15.4 radio module 29, the Bluetooth™ module 31, the microSD card 37, and general purpose I/O ports 35 through data lines. The microcontroller 27 passes data between the radio module 29 and the Bluetooth™ module 31, and it can also intercept the data from the radio module and store it into a microSD card 37. The microcontroller 27 can also take user inputs from buttons and switches on general purpose I/O ports 35, and also output signals to LEDs on general purpose I/O ports 35.

In FIG. 2, an IEEE 802.15.4 radio module 29 receives data sent by the wristband sensor. The module receives the sensor data, and it relays it to the microcontroller 27 via a UART (universal asynchronous receiver/transmitter connection). This data can be sent to the Bluetooth™ module 31 for transmission to other Bluetooth™ enabled devices, or be saved onto a microSD card 37.

In FIG. 2, a Bluetooth™ radio module 31 communicates with the microcontroller 27 via a UART connection, and transmits the data via Bluetooth™ to the nearby Bluetooth™ enabled devices such as computers and smartphones. It is used to provide a more common wireless interface for computers and smartphones, rather than the IEEE 802.15.4 protocol.

In FIG. 2, a microSD card 37 provides data storage options when Bluetooth™ devices are not available. The data received from the sensors via the IEEE 802.15.4 radio module can be stored directly onto the microSD card in the absence of a computer or a smartphone. The microcontroller 27 has firmware for implementing FAT32 file systems, so the data written onto the microSD card can later be transferred to a computer through a USB port using a microSD to USB adaptor, which is much faster than using the Bluetooth™ connection, especially for large data quantities.

In FIG. 2, a general purpose I/O 35 allows user input and output to the hub. The I/O 35 comprises switches that can be used to enable/disable the microSD card storage, and LED outputs can be used to indicate to the user the state of Bluetooth™ pairing. For example, a blue LED may blink while the Bluetooth™ module is in discovery mode, but may be constantly on when a Bluetooth™ pairing is established.

This invention may be implemented with multiple transducers for delivering therapeutic stimuli. For example, a cell phone may have an on-board microphone, display screen and haptic vibrator, each of which transducers may be used to deliver therapeutic stimuli. Or, for example, a user may wear an arm band with multiple transducers that may deliver vibrations or sounds to the user. Alternately, a transducer may deliver a thermal stimuli (e.g., to create a warm, comforting sensation).

Also, this invention may be implemented with multiple hubs. For example, hubs may be located in different rooms of a house or other building.

Likewise, this invention may be implemented with multiple sensors. For example, there may be multiple sensors on different parts of a user's body (e.g., right wrist, left wrist, and upper arm). Or, for example, the sensors may be located on multiple human users. One of the sensors might be co-located with or physically attached to the hub.

In exemplary embodiments of this invention, sensor radio modules do not continuously transmit a stream of data. Instead, a packet based wireless data protocol and wireless channel sharing are employed. These allow multiple sensor radio modules to be operated at the same time. The packet-based protocol allows multiple transmitters to share a channel through either CSMA/CA (Carrier Sense Multiple Access/Collision Avoidance) in the MAC layer, or through a hub-mediated beacon-based time division multiplexed approach, both of which are well known in the field of wireless sensor networks. The wearable sensors implementing the IEEE 802.15.4 radio transmission employ direct-sequence spread spectrum and generally use one of 16 possible 5 MHz channels in the 2.4 GHz ISM band. However, if necessary, multiple frequency channels can be used in orders to improve data throughput or to support a greater number of sensors.

In many cases, a packet-based protocol alone is insufficient to meet the specialized needs of physiological data monitoring because the physiological data must be sampled relatively frequently (~tenths of a second), yet the wireless transmission must occur relatively infrequently (~seconds or tens of seconds). According to principles of this invention, this problem may be solved though the use of a local memory cache. By locally storing and processing the data and then transmitting it in one large burst rather than many short transmissions, protocol overhead is minimized and throughput maximized in the communications channel.

For example, short-term memory storage may be provided onboard the sensor radio modules (e.g. with about 128 Kbytes of EEPROM memory). Or, for example, longer-term data storage may be achieved with a larger capacity flash memory storage (e.g., Gigabytes) onboard a wearable data hub, described below.

In an exemplary implementation of this invention, biosensors may gather data regarding one or more of heart beat, breathing, skin conductance, biopotentials, body core temperature, optical reflectance of blood vessels, or limb movement.

In many applications—such as helping former addicts resist drug cravings, it is desirable for the biosensors to operate on a long-term, round-the-clock basis. In that case, it is desirable for the biosensors to be worn in a comfortable, washable form factor, such as a wristband, armband, ankleband or sock.

Figure 3:
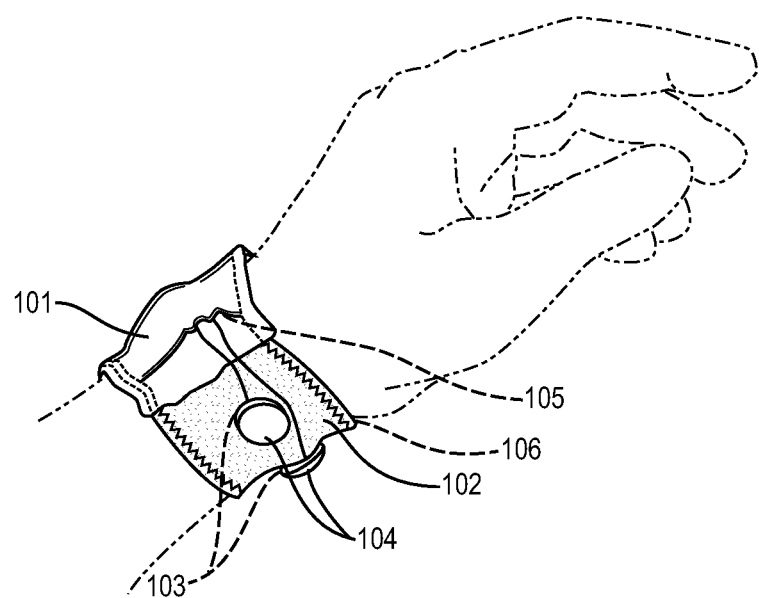
FIG. 3 shows a wrist/hand band with an electrodermal activity (EDA) sensor, in an illustrative implementation of this invention.

FIG. 3 shows an example of a comfortable, wearable biosensor, in an exemplary embodiment of this invention. The sensor measures electrodermal activity (EDA), also known as galvanic skin response. The electrodes for the EDA sensor 103 are made of one or more electro-conductive materials, including conductive fabrics and yarns, conductive polymers, conductive elastomers or metal. For example, the material can be a medical-grade silver-plated 92% Nylon 8% Dorlastan® fabric (Cat. #A251, Less EMF, Inc., Albany, N.Y.). This electro-conductive fabric is washable, allows the skin to breathe, maintains elasticity and provides consistent contact with the skin.

Alternatively, the electrode comprises electro-conductive thread or yarn embroidered into fabric or other material. For example, a stainless steel electro-conductive thread sold by Bekaert (Winston Salem, N.C.) can be used. This enables greater comfort and durability since the conductive thread exhibits less strain fatigue than traditional metal wires. Alternatively, electrically conducting elastomers or polymers may be used for the electrodes. Poly(3,4-ethylenedioxythiophene), also known as PEDOT, is an example of such a conducting elastomer. Carbon-impregnated rubber is an example of such a conducting polymer. These conductive elastomers and polymers are not generally breathable and thus less desirable. This problem may be solved in some cases by aeration (i.e., hole-punching) that makes the material more breathable. For example, carbonized rubber may be aerated in that fashion. Alternatively, standard medical metal electrodes may be used. For example, silver-silver chloride electrodes (such as those commonly used in electrocardiographs) may be used. These provide good contact with the skin. The metal electrodes may be detachably mounted on the fabric using pop-in snaps or the like.

Metal snaps 104 may be used to connect the electrodes (or leads from them) to the circuit (or lead from it). When the snaps are snapped together, the electrodes and circuitry are electrically connected; when they are snapped apart, they are not electrically connected. These snaps thus enable the circuitry to be repeatedly attached to and detached from the wearable band with electrodes. The wearable band with electrodes can then be easily washed or replaced. The placement of the metal snaps 104 may vary. For example, the snaps may be near the electrodes, or near the circuitry instead. Alternatively, other electrical connectors may be used instead of the metal snaps. In some implementations, the electrical connector is light-weight and at least one part of the connector is washable.

In the example shown in FIG. 3, the circuitry for the EDA sensor 105 fits, and is secured, within a hydrophobic pouch on the band. This protects the circuitry from contact with the wearer, liquids or other external objects.

In FIG. 3, a hydrophobic, breathable material 101 is used to form the pouch for circuitry, and to form parts of the wearable band. For example, this material 101 may be Gore-Tex® (sold by W. L. Gore & Assoc., Newark, Del.). Or, for example, the material may be Dryline® (sold by Milliken & Company, Spartanburg, S.C.). This stretchable fabric is hydrophilic on the inner layer and hydrophobic on the outer layer, so that moisture moves away from the wearer's skin through the fabric to the outer layer, where it evaporates. Alternatively, other hydrophobic, breathable materials may be used. For example, eVent® fabric (sold by BHA Group, Inc., Kansas City, Mo.) or Epic® fabric (sold by Nextec Applications, Inc., Bonsall, Calif.) may be utilized. Fabrics comprising a mix of elastic and leather may also be used to advantage.

In the example shown in FIG. 3, the electrodes are hosted by a flexible, breathable material 102. In some embodiments, a synthetic stretch mesh, such as 85% nylon and 15% Lycra® blend, is used. In some embodiments, the material used in 102 may be the same as the breathable, hydrophobic material used in 101.

A flexible closure 106 is used to fasten the two ends of the band together. For instance, the flexible closure may comprise Velcro® strips and a metal snap fastener.

The wrist is not a conventional location for measuring EDA since the sweat glands there tend to be less sensitive than those on the palm or fingers, where EDA is traditionally measured. This issue, coupled with the use of dry electrodes, means that in this example it may take at least 15 minutes (depending on humidity and the individual's temperature) before the moisture buildup between the skin and electrodes is sufficient to show a range of responsiveness on the wrist. The main advantage of sensing EDA from the wrist is that the sensor can be comfortably worn for long periods of time (days and weeks) by adults and by small children (ages 3-6) without interfering with daily activities, such as sleeping, washing hands, or typing. If desired, the wrist-worn strap can be slid up onto the palm for a more sensitive EDA response.

Figure 4:
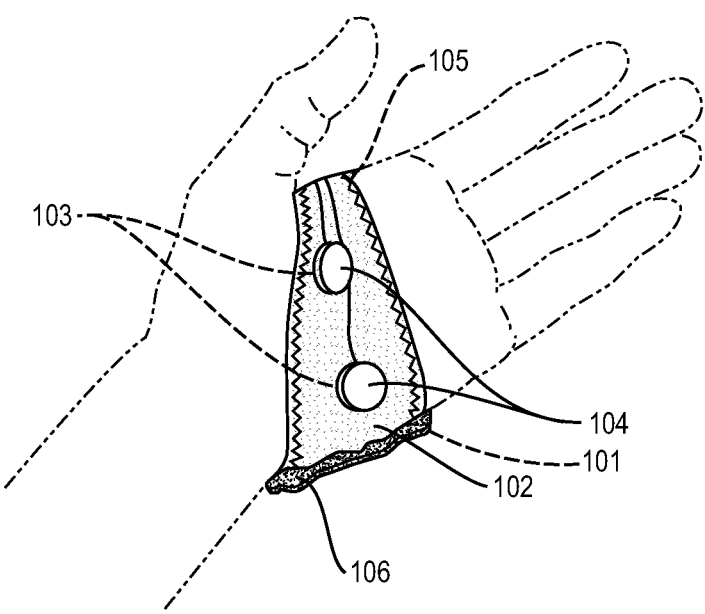
FIG. 4 shows the same band, being worn on the hand/palm, in an illustrative implementation of this invention.

FIG. 4 illustrates the same wearable band with EDA sensor as that in FIG. 3. However, in FIG. 3, the band is being worn on the wrist; whereas in FIG. 4, it is being worn on the hand/palm.

Figure 5:
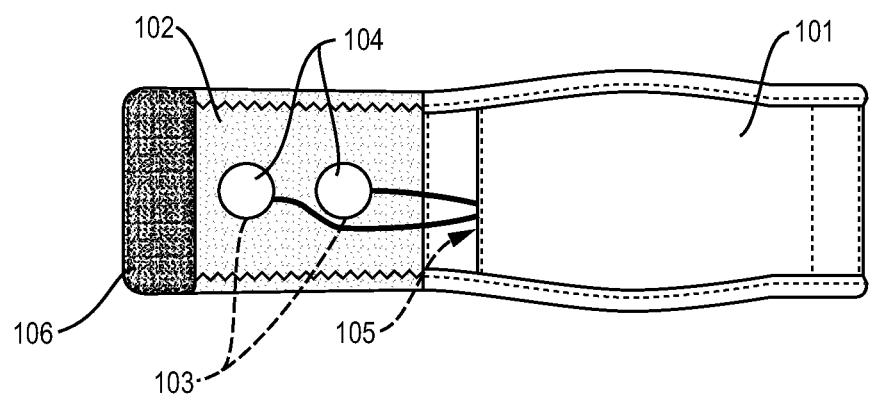
FIG. 5 shows an outer side of the same band, in an illustrative implementation of this invention.

FIG. 5 shows the exterior of the same band.

Figure 6:
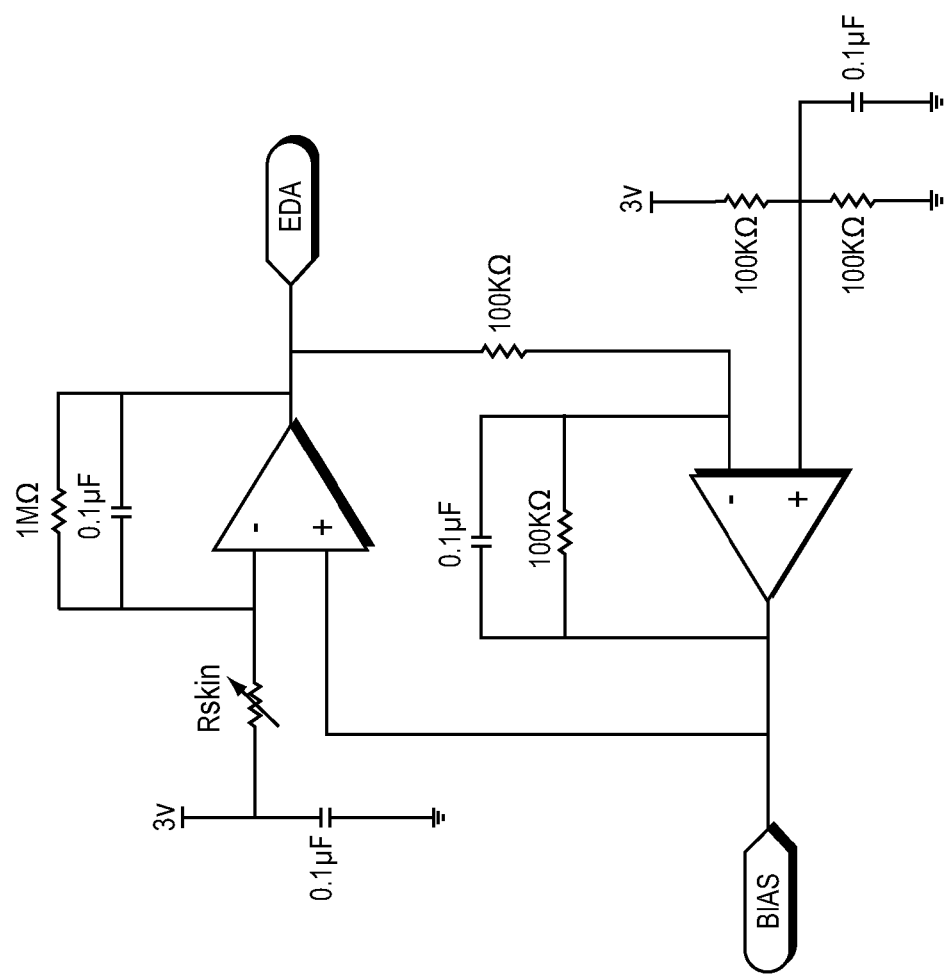
FIG. 6 is a schematic of a sensor circuit used to measure EDA, in an illustrative implementation of this invention.

FIG. 6 is a schematic of a biosensor circuit used to measure electrodermal activity (EDA), in an illustrative implementation of this invention. The EDA sensor module implements an exosomatic measurement of EDA, such that a small voltage is applied to the skin and the resulting potential drop is measured. The primary technical challenge in creating this circuit was to achieve a low-power design while still maintaining good dynamic range. It is well known that baseline skin resistance can vary over a few orders of magnitude from 100 KOhms to approximately 10 MOhms; yet, it is necessary to detect minute changes in this value. Greater dynamic range and sensitivity could be achieved by increasing the voltage rails. In the example shown in FIG. 6, however, 3 Volts is chosen for the positive voltage rail in order to minimize power consumption and allow interfacing to low-power radios.

Alternately, the EDA sensor circuit may be implemented using a digitally controlled variable gain amplifier to maximize dynamic range. However, this requires the use of an external microcontroller that adds greater cost, complexity, and power consumption.

Figure 8:
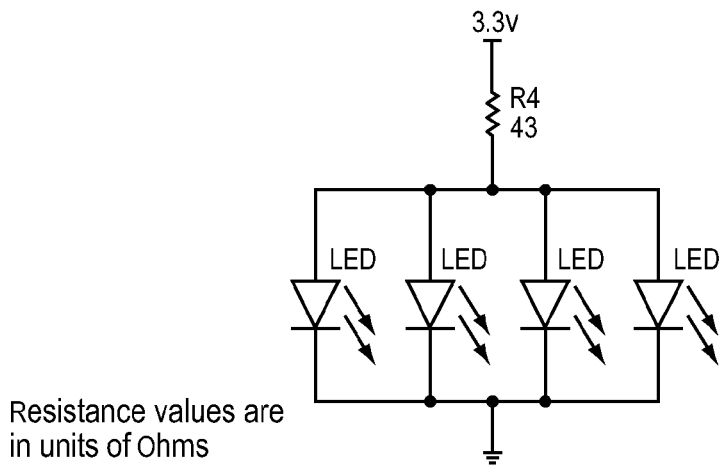
FIG. 8 is a schematic for a linear strip of LEDs, which strip is part of a photoplethysmograph (PPG) heart rate sensor, in an illustrative implementation of this invention.

In the example shown in FIG. 8, the EDA circuit includes an op-amp circuit with non-linear feedback that automatically scales gain to compensate for the large range in skin conductance. In this example, use of an op-amp with a low-leakage current (such as the AD8606, Analog Devices, Inc., Norwood, Mass.), achieves a measurement circuit with wide dynamic range and low power consumption (<1 mA at 3V). Other approaches can also be used to address the need for large dynamic range, including transistors or diodes in the op-amp feedback circuit or using a digitally-controlled programmable gain amplifier.

In some embodiments of this invention, an EDA circuit performs a time-domain measurement of skin conductance by employing an oscillator circuit whose oscillation frequency is dependent on the skin conductance. By measuring this frequency instead of measuring the skin resistance directly, it is possible to perform a more precise measurement given the low power rails and limited dynamic range of the voltage.

In order to maximize battery life and maintain a stable voltage rail for the op-amps and sensors, a low-power low-noise regulator (LM1962, National Semiconductor, Santa Clara, Calif.) may be added. This regulator has a power enable pin that can be used to only momentarily provide power to the sensor module and power it off when it is not in use, thereby reducing the power consumption of the entire EDA sensor module to less than 20 microwatts.

Figure 7:
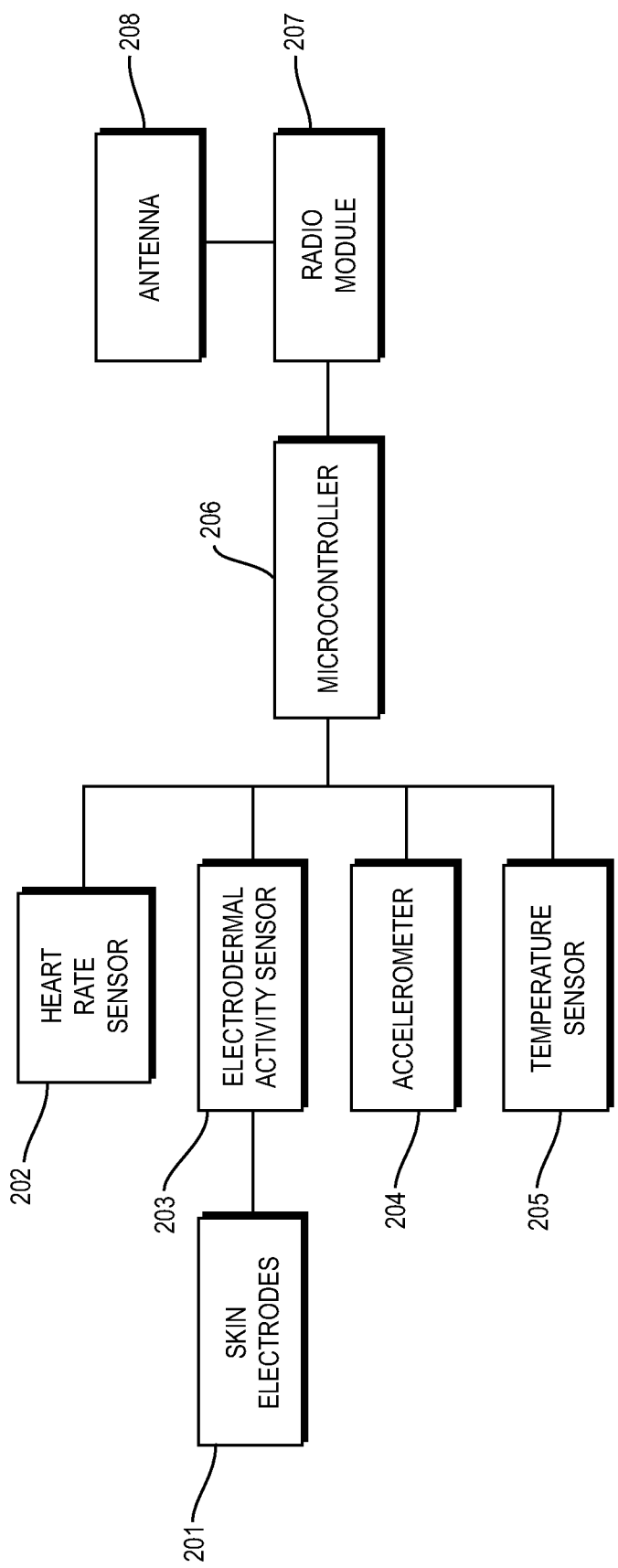
FIG. 7 is a block diagram of a wearable biosensor, in an illustrative implementation of this invention.

FIG. 7 is a block diagram of a wearable biosensor that has multiple sensors 202, 203, 204, 205, in an exemplary embodiment of this invention. The wearable biosensor also includes a microcontroller that processes data from the sensors 206, a radio module 207 and antenna 208. The radio module and antenna are used solely for transmission in some embodiments and operate as a transceiver in other embodiments. The multiple sensors may include, for example, an EDA sensor 203, a heart rate sensor 202, accelerometer 204 and temperature sensor 205. In this example, electrodes 201 for the EDA sensor are included.

This invention may be implemented with a wearable biosensor that includes at least one photoplethysmograph (PPG) for measuring heart rate (HR) and heart rate variability (HRV). Since the light absorption of blood is wavelength dependent, if two different wavelength LEDs are used, then it is also possible to measure the relative blood oxygen level using the ratio of readings between the two color LED's.

Conventional PPG devices employ a single LED light. However, this invention may be implemented with a PPG device that has multiple LEDs. FIG. 8 is a schematic of an array of LEDs in a PPG sensor, in an illustrative implementation of this invention. Multiple LEDs are desirable for a PPG in a wearable device, in order to minimize noise and error due to motion, inexact placement, and slippage of the wristband over the blood vessels.

In some embodiments of this invention, a PPG photodiode absorbs light reflected from the skin. In other embodiments, a PPG photodiode absorbs light transmitted through tissue.

Figure 9:
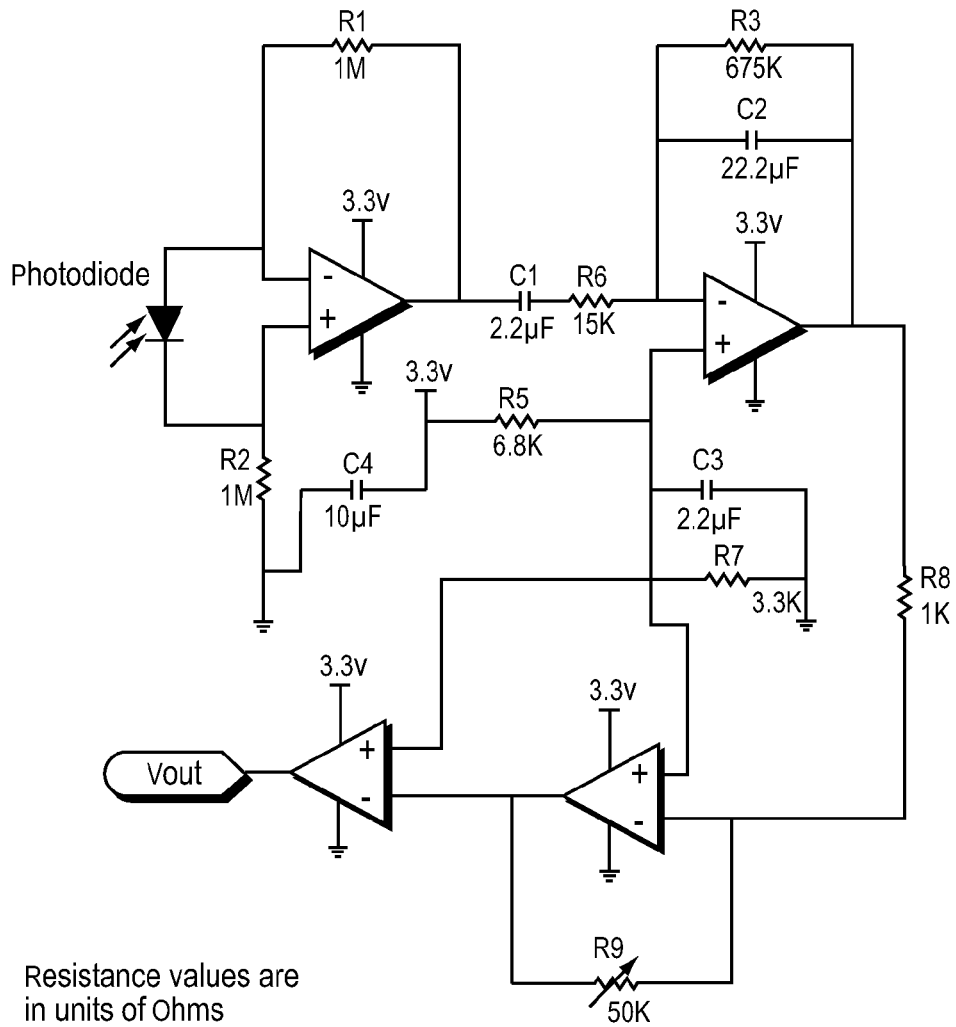
FIG. 9 is a circuit schematic for a heart rate sensor, in an illustrative implementation of this invention.

FIG. 9 is a schematic of a photodiode and PPG sensor circuit, in an illustrative embodiment of this invention. In this example, the PPG is designed to be low-power and low-cost. As such, a rail-to-rail operational amplifier with a high slew rate, a low input bias current ($I_{IB}$), a low minimum operating voltage, a gain bandwidth higher than 0.9, an Iq less than 1 mA, and a low price is desired. For example, a TLV2784 op amp (Texas Instruments, Dallas, Tex.) may be used as the operational amplifier in the PPG sensor because it meets all of the aforementioned requirements: rail-to-rail input and output, a minimum operating voltage of 1.6 V, a high slew rate of 4.3 V/uS, $I_{IB}$ of 15 pA, Iq of 0.82 mA per channel, a gain bandwidth of 8 MHz, and a low price. The PPG sensor's output signal varies with respect to blood volume and consists of two peaks. The large, periodic peaks present in a PPG signal lag behind the R wave (of the QRS wave complex of an electrocardiogram), occur at the same frequency as R waves and can therefore be used for calculating heart rate, heart rate variability (HRV) or vagal tone For ease of reference, "R wave peak" means the main (large, periodic) peak in a PPG wave. The smaller, secondary peaks in a PPG wave correspond to venous pulsations.

Figure 12:
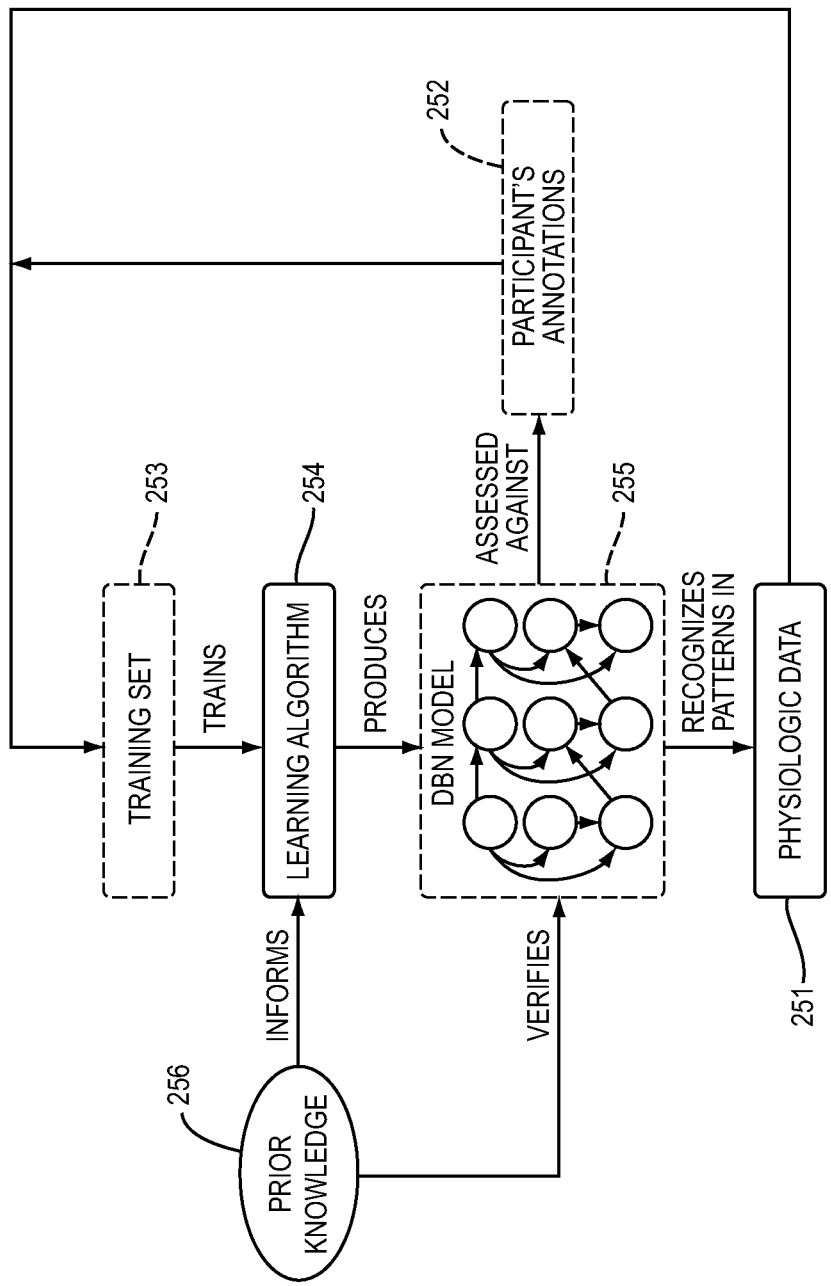
FIG. 12 is a block diagram of high-level functionality of a learning machine that employs Dynamic Bayesian Networks, in an illustrative implementation of this invention.

In the example shown in FIG. 12, the PPG circuit has four stages:

The first stage of the circuit is a transimpedance amplifier, which converts the current produced by the photodiode into voltage. A 1 MΩ resistor is placed at the positive input of the op-amp because it doubles the value of the input signal without doubling the gain.

The second stage is a bandpass filter with corner frequencies 4.8 Hz and 10.6 Hz, a bias voltage of 1.08 V, and a gain of 45. The low cutoff value was chosen because it eliminated the DC bias and removed baseline frequencies without deforming the QRS complex of the heart beat. Since this is only a first order filter, the high cutoff value was chosen at 10 Hz to ensure the elimination of 60 Hz noise. This simple RC first order filter was implemented instead of more complicated higher order filters to minimize the noise introduced by additional stages. Since within the QRS complex, the R wave has higher amplitude than both the Q and S segments, the bias voltage was set a bit lower than 1.65 V, which is half of $V_{cc}$, to prevent signal saturation.

The signal obtained via PPG on the wrist has very small amplitude; therefore, a high gain is necessary in order to place the sensor's output signal within the proper range so that the microcontroller can detect the R wave peaks. The value of this gain, however, varies from user to user. For instance, a male adult with thicker skin will need a higher gain than a child with small wrists. A 50 KΩ wheel potentiometer was placed in the third stage of the PPG heart rate sensor in order to enable users to adjust the gain so that the signal falls within the proper range. A wheel potentiometer, as opposed to a rotary potentiometer or a rheostat, was chosen so that the user would be able to easily adjust the gain without the use of a screw driver or similar tools.

The fourth stage of the PPG heart rate sensor is a buffer with a bias of 3.3 V. Since the output of the third stage is an inverted heart beat signal, a purpose of the buffer is to invert the signal so that the output of the overall circuit properly represents a heart beat signal. It is desirable that the output has the correct polarity so that the comparator in the microcontroller can properly detect the R wave peaks. The output of the heart rate sensor is then connected to an 8-bit microcontroller, specifically an ATmega168 (Atmel Corporation, San Jose, Calif.), which detects the R wave peaks in the signal. It operates very similarly to a comparator: when the input signal is higher than 1.5 V, it counts it as beat and ignores the signal as it decreases back to its baseline value. As the R wave peak reoccurs, the signal increases yet again. As it crosses the 1.5 V threshold, the microcontroller records another beat. It then subtracts the two obtained time stamps to determine the time between the two R waves. Next, the time difference values between ten consecutive R waves are averaged and used to calculate the user's heart rate. As such, in this example, it is desirable to adjust the gain in the third stage of the circuit to a value such that the R wave peak crosses the 1.5 V threshold level. In many cases, the gain should not set too high, so that the amplitude of the input signal's other components remains below 1.5 V. For instance, if the gain is too high, then (a) the R wave could be saturated at 3.3 V while the smaller, secondary PPG waveform also crosses the 1.5 V threshold, and (b) the microcontroller, in turn, could count both waveforms in determining the user's heart rate and could produce a heart rate value that is too high.

Alternately, the EDA sensor circuit, PPG sensor circuits and LED circuit could be designed in other ways than the implementations described above.

This invention may be implemented in such a way that one or more motion sensors are included. For example, an analog motion sensor (SQ-SEN-200, Signal Quest, Lebanon, N.H.) with an integrator circuit may be used. Advantages of this analog sensor, over a 3-axis accelerometer, are that it draws less than 1 microamp of current and is inexpensive to purchase. Alternatively, various types of motion sensors may be used, including 3 axis digital accelerometers. For example, the motion sensor may be any of various types of micro electro-mechanical systems (MEMS) consisting essentially of a proof mass on a damped spring, that measure the deflection of the proof mass in an analog or digital manner. For example, the deflection may be measured by piezoresistors attached to the spring, or by changes in capacitance between fixed beams and beams attached to the proof mass. Also, for example, the accelerometer may have a small heated dome of gas and measure the deflection of the center of the dome.

A motion sensor can also be used to gate the PPG signal so that heart rate data during motion can be ignored or cleaned. It should be noted, however, that there are many times during the day or night when a person's wrists are still, thus allowing for snapshots of HR and HRV. The combination of motion, EDA and HR/HRV are particularly relevant for recognizing sleep stages and conditions such as apnea. In some embodiments, multiple PPG sensors are employed. The multiple PPG signals are combined using signal processing, which reduces noise caused by motion artifacts. In some versions of the invention, logarithmic detection is used, which also helps handle motion artifacts.

The wearable biosensor may include a temperature sensor. For example, a low-power temperature sensor (LM60, National Semiconductor, Santa Clara, Calif.) is used.

This invention may be implemented in such a way that one or more sensors (such as PPG heart rate sensors, motion sensors and temperature sensors) are removable in their entirety from the wearable biosensor. This allows the sensors to be easily removed or replaced, for example, when the band or other host material for the sensor is washed. In other embodiments, one or more of these sensors are coated in plastic or another waterproof or water-resistant material, so that they can remain with the wrist band (or other wearable garment or material) when it is washed. In the case of PPG sensors, this coating is preferably transparent to the wavelength of light (including red or infrared light) emitted by the LEDs and absorbed by the photodiode. In the case of any temperature sensor, this coating preferably has a high thermal conductivity. In versions where these sensors remain with a band (or other wearable garment or material) when it is washed, leads may be used to connect the sensors with the removable circuitry, including the radio module and antenna. Metal snaps or other electrical connectors may be used to enable the sensors (or leads from them) to be repeatedly attached to or detached from the removable circuitry (or leads from it).

In some embodiments, rechargeable batteries are used to power the sensors. This not only eliminates the need to purchase hundreds of batteries that may be needed for long-term use, but enables the battery to be completely embedded inside the wearable package for weatherproofing and safety reasons (e.g., for infant use).

In some embodiments, the biosensors also include a low-power radio module and antenna, and transmit using a wireless protocol that is appropriate for low-power radio hardware. For example, the biosensors may transmit using the IEEE 802.15.4 protocol.

In some implementations of this invention, the Zigbee radio protocol is used for the sensor radio modules. Zigbee is a multi-hop transport protocol based on the IEEE 802.15.4 physical layer protocol.

Although higher-level transport protocols such as Zigbee support multi-hop routing and mesh networking, some implementations of the invention adopt a star topology for the network in order to minimize processing overhead and power consumption. This radio hardware also provides a wireless operating range of 25 meters.

Some conventional wireless sensors operate in the UHF range, e.g. 433 MHz, 915 MHz. However, this invention may be implemented with sensor radio modules that operate with 2.4 GHz in order to enable a smaller antenna size and achieve better indoor radio propagation.

In some embodiments, the sensor radio module comprises an ATmega168V microcontroller (Atmel Corporation, San Jose, Calif.) and a Chipcon CC2420 RF transceiver (Texas Instruments, Dallas, Tex.). In some versions, the sensor radio module exposes six 10-bit A/D ports on the microcontroller for interfacing with the sensor module. The reference voltage on these inputs can be configured via wireless commands from an external device. In some embodiments, a processor on-board the sensor can map patterns of the physiological and motion data to signals or alerts such as a likely seizure, drug craving, or other states that the wearer would like to know about or use to alert other people or devices for assistance. Alternatively, pattern analysis can be performed in a device that directly or indirectly receives the wireless data.

This invention may be implemented in such a way that an IEEE802.15.4 sensor radio module has firmware with independent sampling and transmission intervals that can be set via wireless commands from an external device. For example, every transmission cycle, the radio module may wake up and then in turn activate the power enable pin on the sensor module to power up the sensors. After a 10 ms delay, the radio module may capture a 10-bit A/D sample from each of the sensors, transmit the data packet wirelessly, and then go back to sleep. Alternately, data samples from sensors may be stored in a cache or buffer before being transmitted.

In some implementations, to reduce cost and provide omnidirectional performance, a sensor has an integrated printed circuit board antenna. For example, some embodiments employ a bent-dipole, horseshoe-shaped antenna that results in a compact design having a nearly isotropic radiation pattern.

IEEE 802.15.4 communication hardware supports a 250 kbps data rate. However, since EDA data has a relatively low rate of change, it is desirable in some implementations to use a slow sampling rate of 2 Hz and packetized data transmission to allow a very low operational duty cycle and long battery life.

This invention may be implemented in such a way that sensor radio modules employ channel-sharing wireless protocols to enable the transmission of data from multiple users and multiple sensors (e.g., both sides of the body, wrists or hands and feet, or multiple people). For example, as part of the firmware implementation of the IEEE 802.15.4 MAC (Media Access Channel) Layer, the CSMA (Carrier Sense Multiple Access) algorithm may be employed. This algorithm provides exponential back-off in the case of colliding transmissions between two or more radio modules. Different types of the CSMA protocol may be used in the invention, including 1-persistent, p-persistent and non-persistent CSMA. Alternatively, other contention network protocols may be used. For example, any of the following protocols may be used to avoid or reduce data collisions in the wireless network: TDMA (time division multiple access), slotted ALOHA, reservation ALOHA, OFDMA (orthogonal frequency-division multiple access), and MACA (multiple access with collision avoidance).

In an illustrative implementation of this invention, the sensor radio module includes a CC2420 radio IC with a maximum transmission power of 1 milliwatt (0 dBm). This provides a wireless detection range of 50-75 meters in free space using a 5 dBi gain receiver antenna. Indoor range is significantly less and depends on the building layout, but is approximately 15-20 meters for the module with integrated antenna and 5-10 meters for the version with external antenna. These wireless operating distances are sufficient for many applications, including transmission to a hub that is being worn by the same person that is wearing the transmitting biosensor. The sensor radio module may also have controllable output power, so the operating distance can be reduced to less than 1 meter as one of several ways to address data privacy. Alternatively, sensor radio modules may employ one or more ICs other than the CC2420.

Privacy and data security are important concerns in many applications. In addition to controlling the radio output power, the CC2420 radio IC includes hardware support for 128-bit AES encryption, which can be turned on as an option. In some implementations of this invention, a sensor device contains a user controlled ON/OFF switch so the user can choose to turn off the data transmission when desired.

In exemplary implementations of this invention, after a hub receives data from sensor radio modules, the hub transmits the data to a Bluetooth™-enabled device. From there, the data is transmitted directly or indirectly to a computer. A variety of different wireless or wired networks may be used for these transmissions, as discussed in more detail below.

After the computer receives the data, at least one processor in the computer analyzes the data in real time, using pattern recognition algorithms to identify patterns in the data that indicate the need for therapeutic intervention.

In some implementations of this invention, a simple classification scheme that does not involve machine learning may be used to recognize a data pattern. For example, in such a scheme, data may be classified based on criteria derived by simply averaging or aggregating the physiological patterns of multiple users. This scheme may be modified for a particular user's physiology by adjustment-to-baseline.

However, in many applications, pattern recognition is more accurate if machine learning is used. For example, machine learning allows a classification algorithm to be customized to take into account differences in affect or context, or cross-user differences in physiology (in a more nuanced manner than merely adjustment-to-baseline). Machine learning algorithms learn from a limited number of examples, where the data may be noisy and contain complex patterns which elude human detection.

It must be stressed that use of a learning machine allows a classification scheme to adapt in response to data. In some embodiments, this gives the processor great flexibility to adjust to complex data patterns that may, for instance, vary from user to user or that may vary within a user over different contexts.

In exemplary implementations of this invention, machine learning with Dynamic Bayesian Networks (DBNs) is employed to better recognize patterns in physiological, affective, and contextual data. It is advantageous to use DBNs for the following four reasons:

First, DBNs are well-suited for modeling a complex dynamic system. For example, they can be used to model behavioral states confounded by time-varying comorbidities that may come into play in the moments before drug relapse. DBNs are designed to manage noisy data, unknown quantities and uncertain events. A DBN has the power to describe not only instantaneous correlations among variables, but also how their values change over time.

Second, DBNs can generalize from limited data because the learning algorithm stresses balancing performance with model complexity. An overly complex model might be able to explain a data set (such as continuous physiology monitoring data) perfectly, but fails to generalize because it is explaining the data's idiosyncrasies (e.g., the humidity that day) of the specific data set. By penalizing model complexity, the algorithm finds the simplest acceptable explanation of the patterns—which are more robust to noise in existing data and tend to generalize better to future data.

Third, individual subjects have varying physiology. DBNs are well suited to devising hierarchical models (where data is organized into branching patterns that describe one-to-many relationships) that allow the prediction of physiological changes of an individual person.

Fourth, computation in a DBN is efficient: the time required is linear in the length of the sequence and may be performed in real time. Although the complexity of computation does grow with the complexity of the network, the learning algorithm strives to produce a simple network for generalization performance; as a consequence, computation is kept efficient. Thus, a classifier derived from a DBN performs minimal computation to produce an accurate result. This computational efficiency is particularly advantageous if the processor is deployed onboard a mobile device, such as a cell phone.

This invention may be implemented in such a way that a pattern recognition algorithm incorporates prior knowledge (in addition to training data). For instance, prior knowledge may include knowledge of transformation-invariance or knowledge about the data.

In an illustrative embodiment of this invention, a DBN learning algorithm incorporates prior knowledge into a suitable prior distribution over structures, which guides the search toward models that are physiologically relevant while also favoring simple models. Furthermore, the DBN's conditional probability tables (CPT's) are parameterized in a way that incorporates domain-specific knowledge. In an illustrative embodiment of this invention, cross-validation is used to set the tunable model parameters. In cross-validation, a portion of the data is withheld from training and instead used for testing; this is repeated across the entire data set.

In some implementations of this invention, the result of the learning algorithm is a structure and parameter set for a DBN: while the training data indicates physiology and context associated with prescription opioid cues, the goal is a classifier to predict State X of relapse risk; this corresponds to using the learned DBN with the relapse status node left unobserved. Prediction of this variable is then made using the Belief Propagation (BP) algorithm, a simple message passing algorithm which operates on the learned network. An advantage of using a DBN is that the computation time required for BP is linear in the length of the sequence, and thus presents no obstacle to implementation in a low-power deployable system.

In illustrative implementations of this invention, a learning algorithm can be trained using data to produce a fully specified DBN: the output consists of both the graph structure determining how variables are interrelated, as well as the CPTs that determine how each variable is influenced by its immediate causes in the model. An advantage of using DBNs is that the resulting models are readily interpretable, in contrast to black box approaches such as neural networks.

In illustrative implementations of this invention, user feedback may be part of the data used to train the algorithm. This feedback may be obtained in a wide variety of ways.

For example, in an application to help a user resist a prescription opioid craving, a mobile computing device may display an Annotate Panel and Activity Panel. These panels may be used to gather user feedback, as described below.

Figure 10:
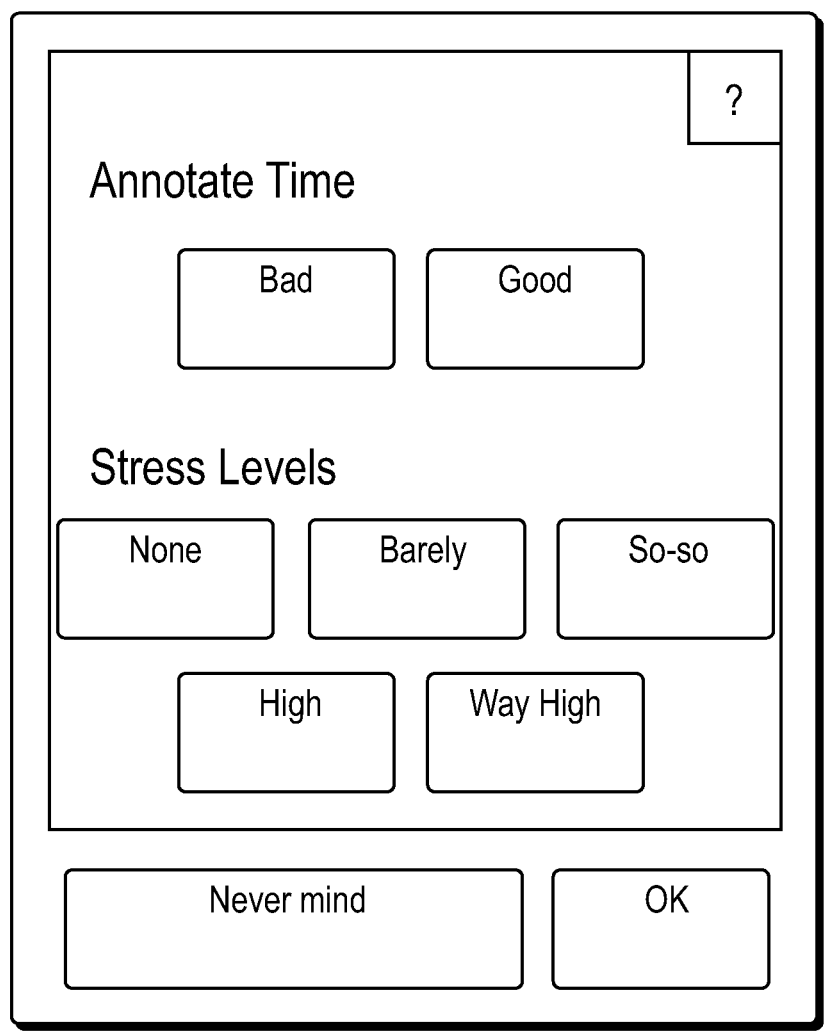
FIG. 10 shows an Annotate Panel for patient self-reporting, in an illustrative implementation of this invention.

The Annotate Panel is a graphical user interface (GUI) comprising multiple screens. It allows users to self-report stress, depression, pain exacerbations, frustration, feeling deprived or the need to reward one's self, prescription opioid craving, or any other feeling, behavior, or event they consider interesting. Color-coded buttons increase recognition and indicate a requested response: Dark Blue-"None" (I don't need anything); Green-"Barely"; Yellow-"So-so" (I can control things); Orange-"High"; Red-"Way High" (I need some help). The Annotate Panel also allows a user to self-report his or her response to relapse prevention interventions. The user enters data for the Annotate Panel on a mobile computing device, so there is no threat of disclosure to another person Annotations can be completed in any location in which the participant has confidence, and all data is securely stored and transmitted. FIG. 10 shows an example of an Annotate Panel. Entering an annotation in a mobile computing device advances the user to an Activity Panel.

Figure 11:
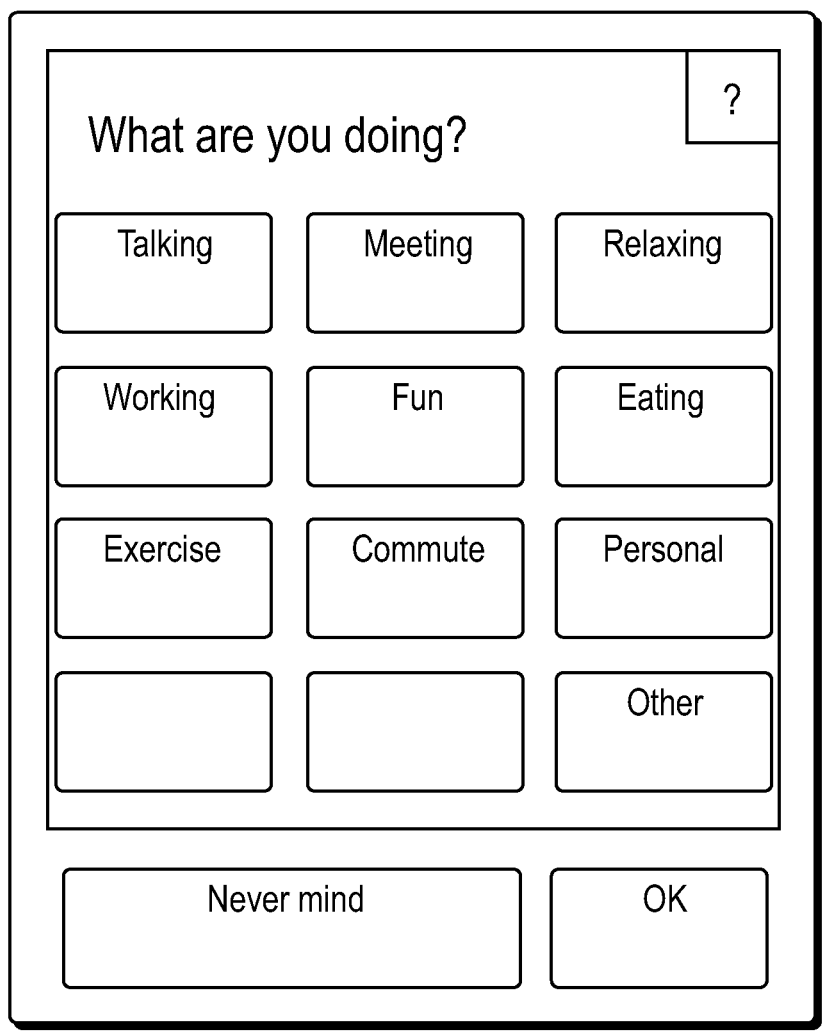
FIG. 11 shows an Activity Panel for patient self-reporting, in an illustrative implementation of this invention.

An Activity Panel is a GUI that allows a user to self-report his or her current activities, such as when experiencing stress. For example, an Activity Panel may allow a user to select Commute, Working, Personal, Fun, Exercise, Relaxing, Eating, Meeting, Talking or Other. After the user selects one of these broad categories, the user is given an opportunity to select a more detailed subcategory. For example, pressing the "Working" button leads to subcategories such as "Argued with boss" or "Just made a sale". In this example, the Activity Panel is generally organized with more popular activities at the top of the screen (and therefore easier to identify by the user). However activities most associated with stress and drug craving are placed in easily recognized locations. FIG. 11 shows an example of an Activity Panel.

FIG. 12 is a block diagram of high-level functionality of a learning machine that employs Dynamic Bayesian Networks, in an illustrative implementation of this invention. Physiological data 251 is received indirectly from sensors. In addition, user annotations 252 are gathered using an Annotate Panel and Activity Panel. The physiological data 251, user annotations 252, and time of day data, repeated over many samples of these data, make up a set of training data 253 that is used to train a learning algorithm 254. The learning algorithm 254 produces a DBN model 255. Prior knowledge 256 is used to inform the learning algorithm 254 and to verify the DBN model 255. The DBN model 255 is employed to analyze physiological data 251 in real time, in order to identify patterns that indicate the need for therapeutic intervention.

Alternately, this invention may be implemented with other approaches to machine learning instead of DBNs. For example, it may be implemented with neural networks, conditional random fields, hidden Markov models, Kalman filters, fuzzy logic, kernel estimation, k-nearest neighbor, learning vector quantization, Gaussian models, RBF (radial basis function) classifiers and other statistical classification approaches.

Figure 13:
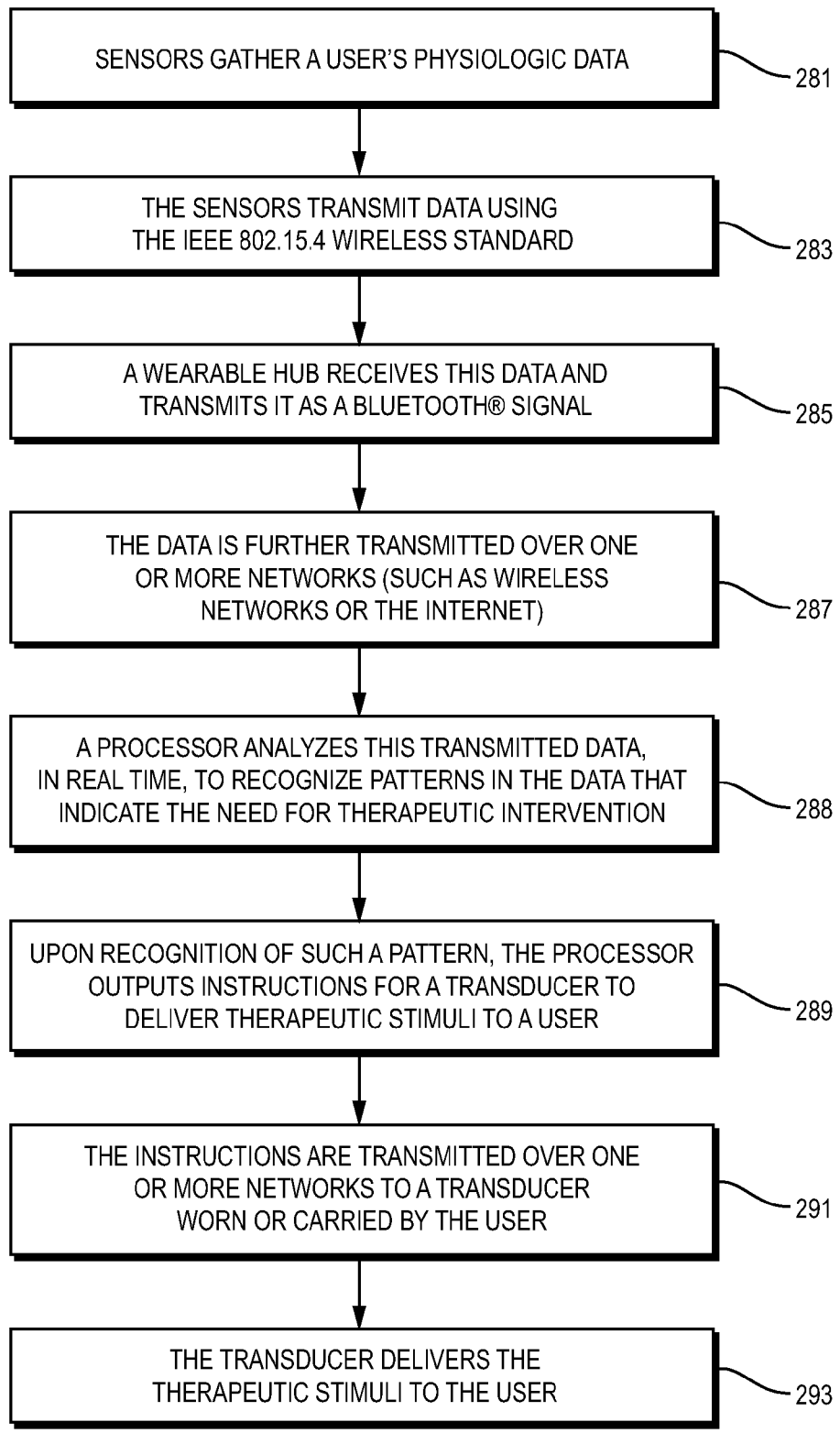
FIG. 13 is a block diagram of steps comprising a method of gathering physiological data and delivering therapeutic stimuli in real time, in an illustrative implementation of this invention.

This invention may be implemented as a method comprising the following steps, as shown in FIG. 13: Sensors gather a user's physiological data 281. The sensors transmit this data using the IEEE 802.15.4 wireless standard 283. A wearable hub receives this data and transmits it as a Bluetooth® signal 285. The data is further transmitted, over one or more networks (such as wireless networks or the Internet) 287. A processor analyzes this transmitted data, in real time, to recognize patterns in the data that indicate the need for therapeutic intervention 288. Upon recognition of such a pattern, the processor outputs instructions for a transducer to deliver therapeutic stimuli to a user 289. These instructions are transmitted, over one or more wired or wireless networks, to a transducer. 291. The transducer delivers the therapeutic stimuli to the user 293. For example, a transducer may deliver the following types of stimuli: visual display of a text message, playing a sound recording, or haptic stimuli such as vibrations or physical nudges.

In exemplary implementations of this invention, one or more wireless networks are employed to transmit data and instructions. If a mobile phone is employed as the wireless hub, the wireless network may be a standard GSM or CDMA network, and the data may be transmitted over 3G or 4G mobile telecommunication data standards, UMTS (Universal Mobile Telecommunications System), or EDGE (Enhanced Data Rates for GSM Evolution). Alternately, this wireless network may comprise a IEEE 802.15.4 network, a Wi-Fi™ network that complies with an IEEE 802.11 standard, or a Wi-MAX network that complies with an IEEE 802.16 standard.

The system architecture may vary, depending on the way in which this invention is implemented. Some examples are shown in FIGS. 14-18.

Figure 14:
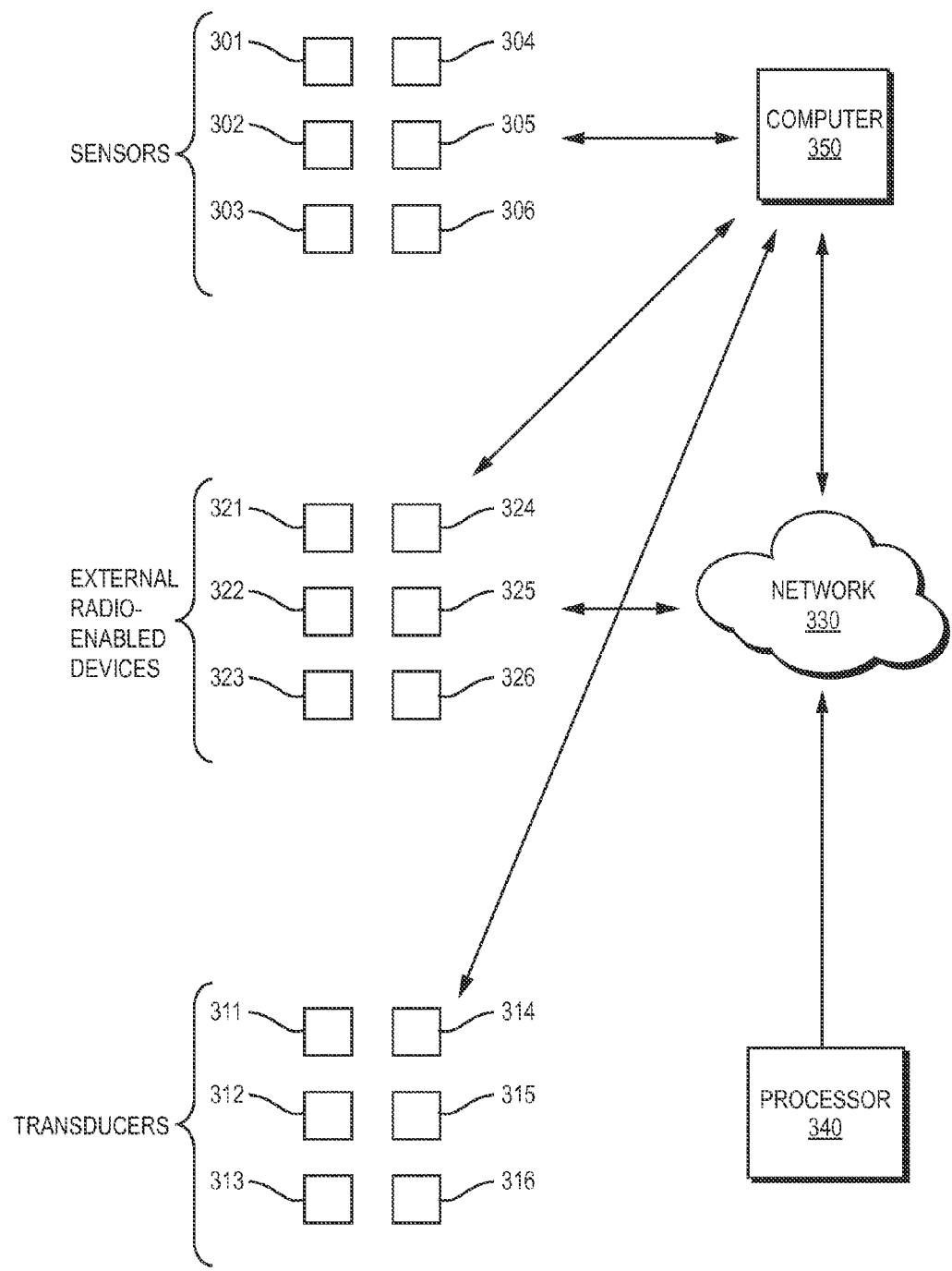
FIG. 14 is a block diagram of system architecture, in an illustrative implementation of this invention.

FIG. 14 is a block diagram that shows system architecture, in an illustrative embodiment of this invention. One or more sensors 301-306 with radio modules may be worn or carried by one or more users. Physiological data gathered by these sensors may be wirelessly transmitted by these radio modules, and received by one or more external radio-enabled devices 321-326. For example, these external radio-enabled devices may comprise, depending on the particular embodiment of this invention, any of the following: a wearable data hub (as described above), a cell phone, a smartphone, a mobile computing device, or a radio base station or reader. These external radio-enabled devices 321-326 may exchange the physiological data with each other. For example, a data hub worn by a user may transmit the physiological data to a cell phone worn by the user. Also, the external radio-enabled devices 321-326 may transmit the physiological data over a network 330, such as a mobile phone network, the Internet or a wired network. Such data may be retransmitted multiple times over one or more such networks 330, until it is received by a processor 340 in a remote computer. For example, this processor 340 may be in a server, a personal computer or a laptop computer. The processor 340 analyzes the physiological data to identify patterns that indicate the need for therapeutic intervention, and outputs directions for transducers to deliver therapeutic stimuli. Alternately, some or all of this processing may be performed by a processor located onboard a sensor 301-306, or onboard an external radio-enabled device (e.g., onboard a smartphone), or onboard a separate (perhaps nearby) computer 350. Alternately, data may be stored in memory onboard a sensor and then transmitted by a wired connection directly to a computer 350, which may process this data itself and/or retransmit this data over a network (such as the Internet) to a processor in an server 340. One or more transducers 311-316 deliver therapeutic stimuli to at least one user. These transducers may be worn or carried by one or more users. Alternately, some or all of these transducers 311-316 may be on-board at least one external radio-enabled device 321-326 (e.g., a microphone, display screen and vibrator onboard a cell-phone). Depending on the particular implementation of this invention, the radio interface for any element of the system may be either a transceiver, a transmitter or transceiver, and communication between the radio interfaces of any two elements may be either one-way or two-way. For example, wireless transmission between a sensor and wearable data hub may be one-way or two-way, depending on the particular embodiment of this invention. For the illustrative system architecture depicted in FIG. 14, the number of elements of a particular type (e.g., sensors, external radio-enabled devices, networks, processors, other computers and transducers) is not set at a particular number, but may vary. For example, there may be only two sensors or 100 sensors, or there may only a wearable data hub and a smartphone, but no other external radio-enabled device. Or there may be no computer (such as a laptop or PC) 350 that is additional to, and separate from, the processor 340 in a remote server, or vice versa.

FIGS. 15 to 18 show other examples of system architectures that may be used, in illustrative implementations of this invention.

Figure 15:
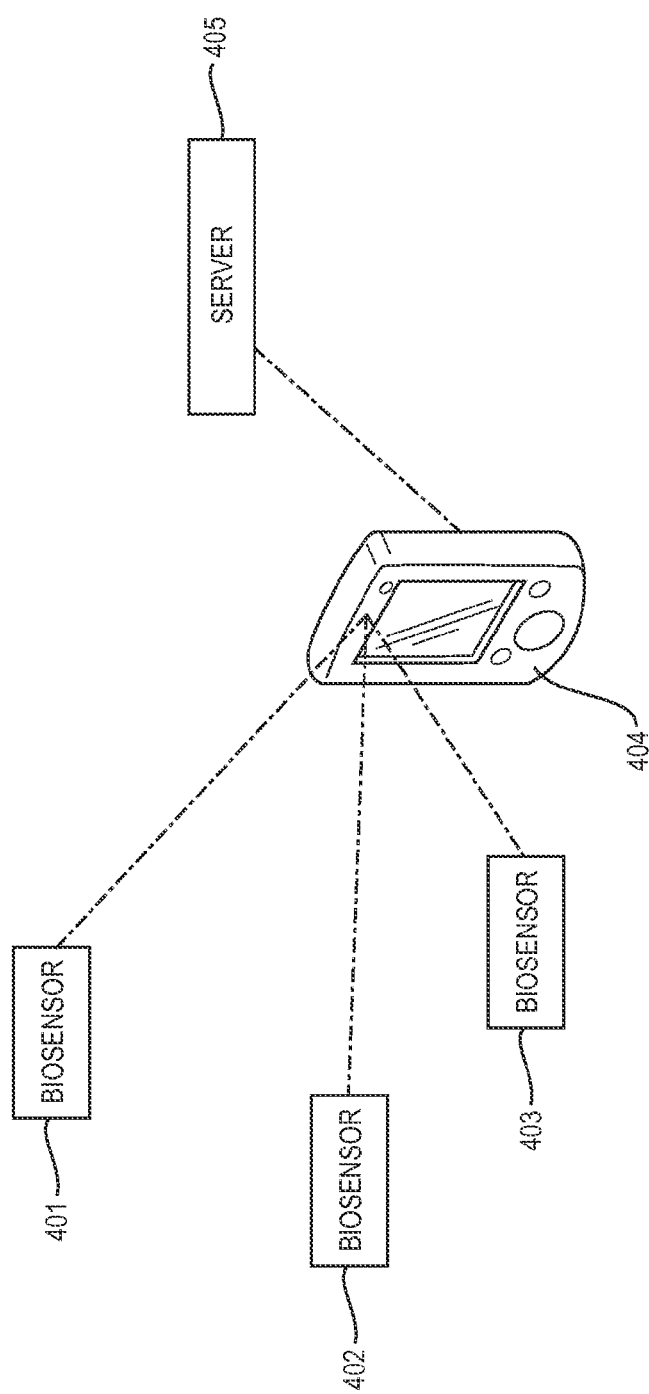
FIG. 15 is a diagram of a different network architecture, in an illustrative implementation of this invention.

In FIG. 15, radio modules in biosensors 401, 402, 403 each have an IEEE 802.15.4 wireless link with a PDA (personal digital assistant) 404. The PDA 404 is linked by Wi-Fi® to a server 405.

Figure 16:
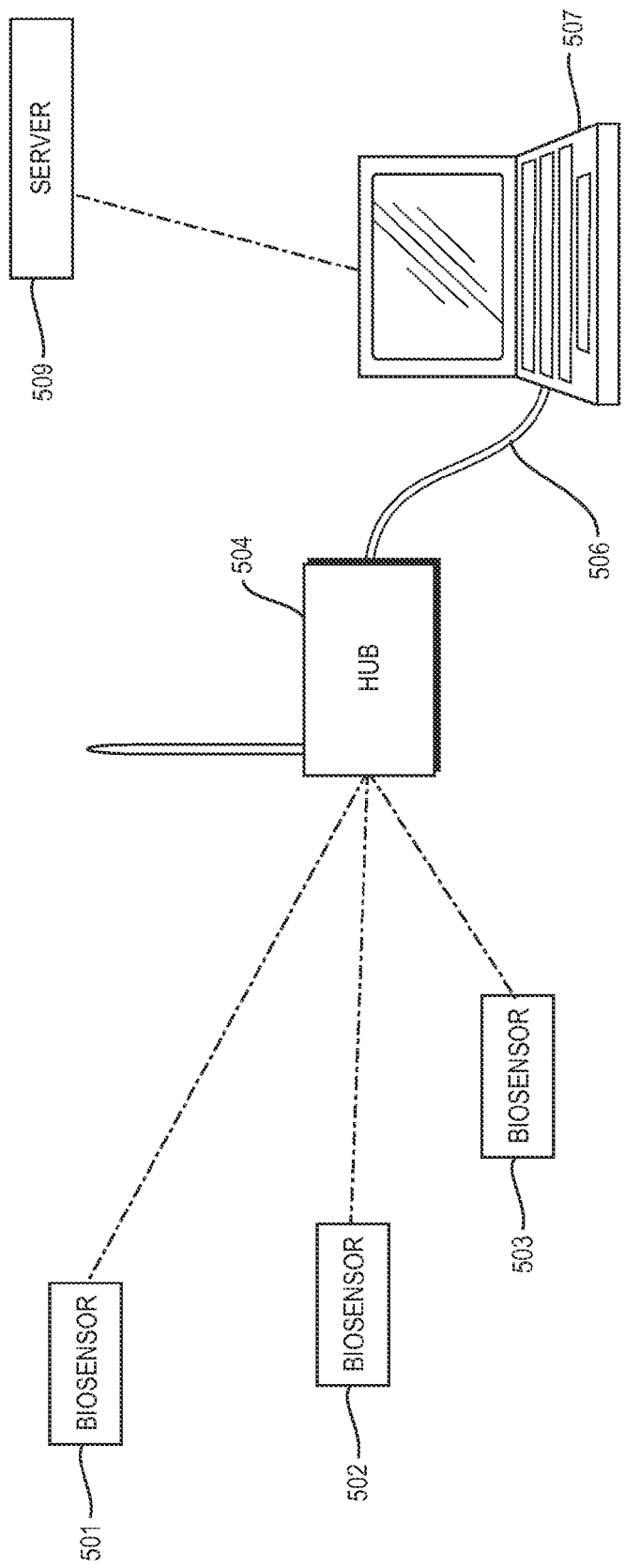
FIG. 16 is a diagram of a different network architecture, in an illustrative implementation of this invention.

In FIG. 16, radio modules in biosensors 501, 502, 503 each have an IEEE 802.15.4 wireless link with a ZR-USB hub 504, described in more detail below. The ZR-USB hub 504 is linked by USB cable 506 to a laptop computer 507. The laptop computer 507 has a Wi-Fi®, ethernet or Internet link to a server 509.

Figure 17:
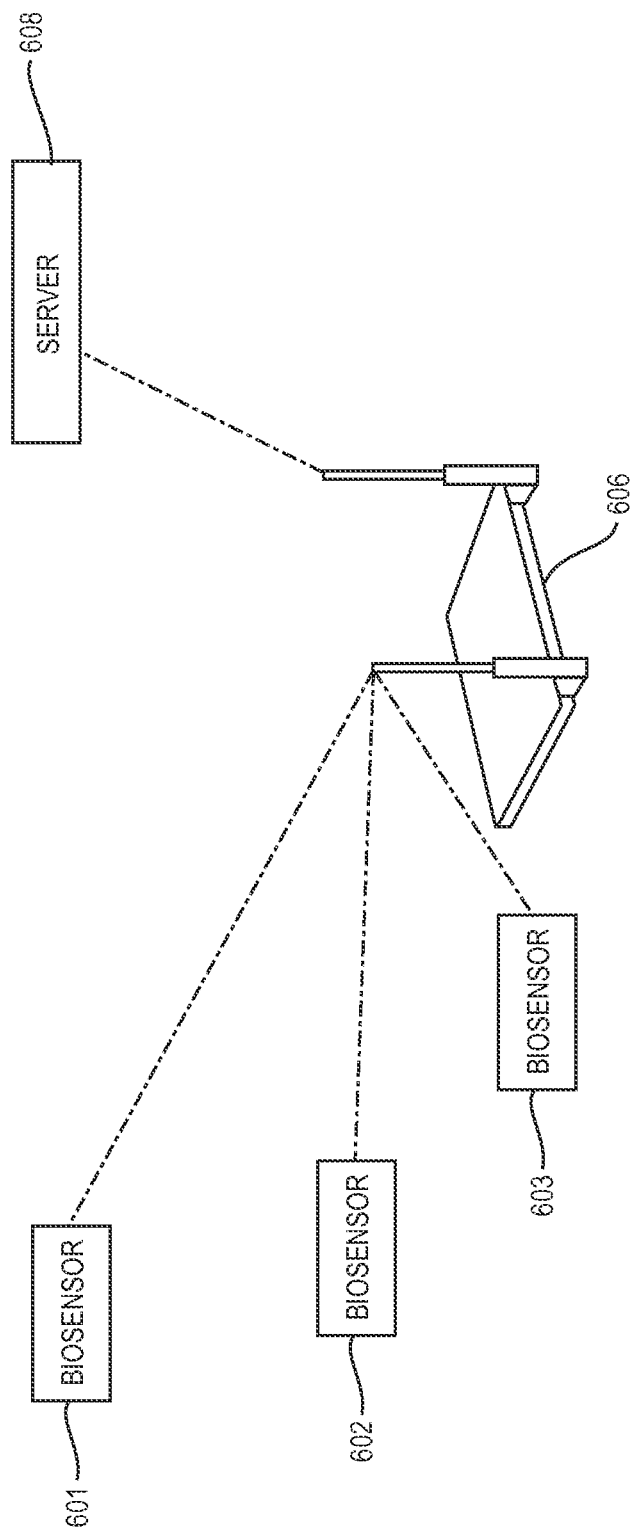
FIG. 17 is a diagram of a different network architecture, in an illustrative implementation of this invention.

In FIG. 17, radio modules in biosensors 601, 602, 603 each have an IEEE 802.15.4 wireless link with a radio base station 606. The base station 606 is linked by Wi-Fi® to a server 608. This base station may use an embedded Linux computer that is uploads data automatically to a remote web server, and is capable of running application-specific programs. In some implementations, the base station 606 is a ZR-HUB.

Figure 18:
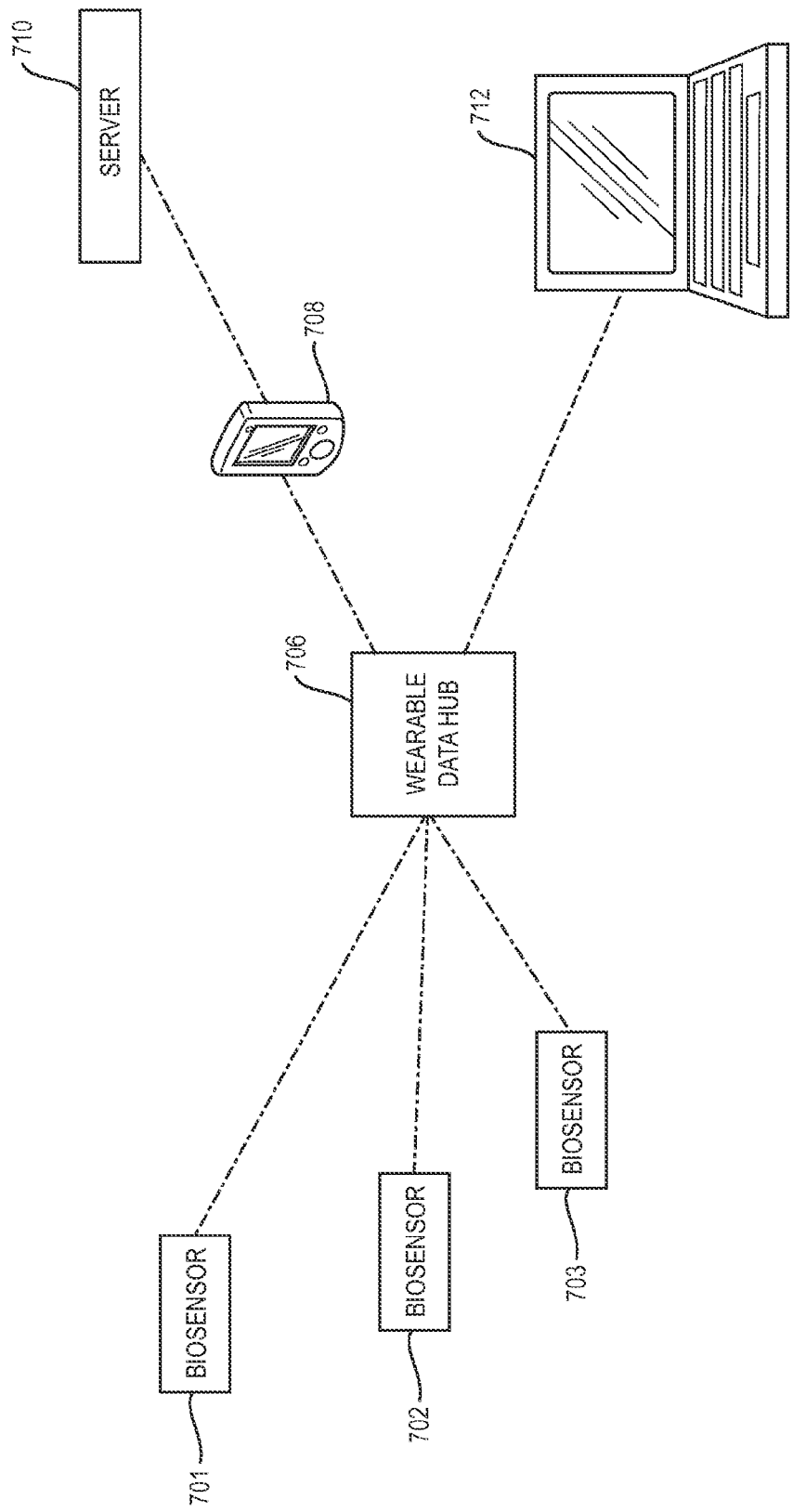
FIG. 18 is a diagram of a different network architecture, in an illustrative implementation of this invention.

In FIG. 18, radio modules in biosensors 701, 702, 703 each have an IEEE 802.15.4 wireless link with a wearable data hub 706. The wearable data hub 706 is linked by Bluetooth® to a smartphone 708, which is linked by GPRS/3G (General Packet Radio Service, $3^{rd}$ Generation) to a server 710. The wearable data hub 706 is also linked (by a wireless or wired connection) with a PC laptop 712.

Figure 19:
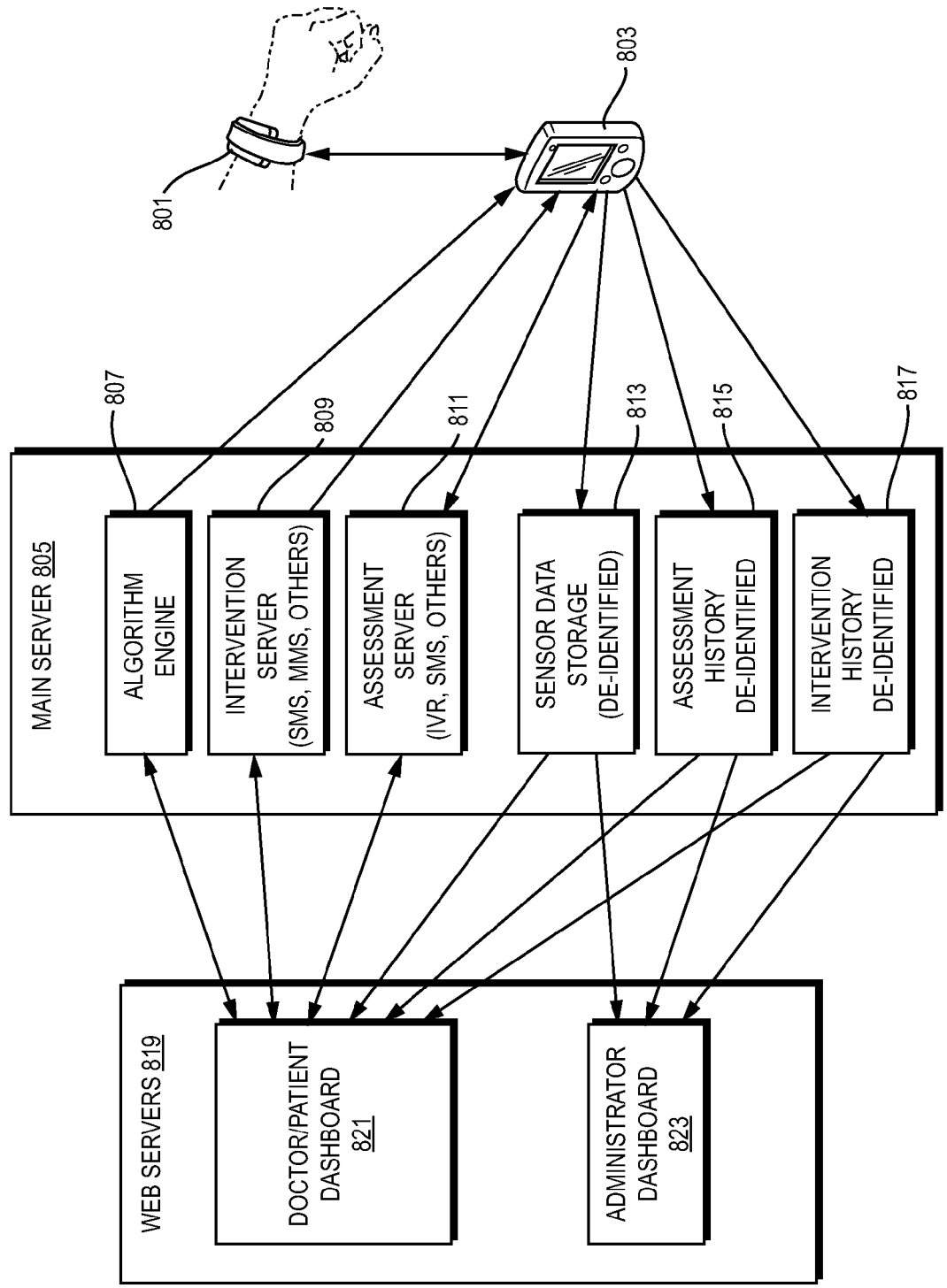
FIG. 19 is a diagram of a different network architecture, in an illustrative implementation of this invention.

This invention may be implemented as shown in FIG. 19. In the example shown in FIG. 19, a sensor module in a wristband 801 measures physiological data and wirelessly transmits that data to a smartphone 803 (such as a smart phone). A main server 805 has an algorithm engine 807. The algorithm engine is a software module that, among other things, performs machine learning to revise a pattern recognition algorithm and maintains the updated classifiers used for interventions. This algorithm engine may be continuously fed with patient data. A revised pattern recognition algorithm may be sent wirelessly to the smartphone 803 (updated daily, for example). The smartphone 803 may run this algorithm locally with data input from the sensor module in the wristband 801.

In the example shown in FIG. 19, a main server 805 also has an intervention server 809. This intervention server is a software module that generates instructions for therapeutic stimuli (e.g., audio, video, text messages, SMS or MMS). These instructions may be sent to the smartphone 803 periodically, so that the smartphone 803 delivers these stimuli periodically (e.g., daily, hourly or weekly). Also, the intervention engine may generate instructions for therapeutic stimuli in response to the recognition of a particular pattern in physiological data.

In the example shown in FIG. 19, a main server 805 also has an assessment server 811. This assessment server is a software module that generates periodic (e.g., daily) surveys. These may show up on the smartphone 803 as a multiple choice question. This can also be down via IVR (interactive voice response) which can automatically call a patient (e.g., robocall) or the patient can call in.

In the example shown in FIG. 19, a doctor/patient dashboard 821 and an administrator dashboard 823 may run on web servers 819. Doctors or patients may use the doctor/patient dashboard to revise parameters in the algorithm engine, intervention server or assessment server.

In the example shown in FIG. 19, a main server 805 may store data in memory, including data from which personal identification regarding particular patients has been removed. The anonymous data that is stored on a main server 805 may include de-identified sensor data 813, de-identified assessment history 815, and de-indentified intervention history 817. This anonymous data may accessed by a system administrator using an administrator dashboard 823.

Figure 20:
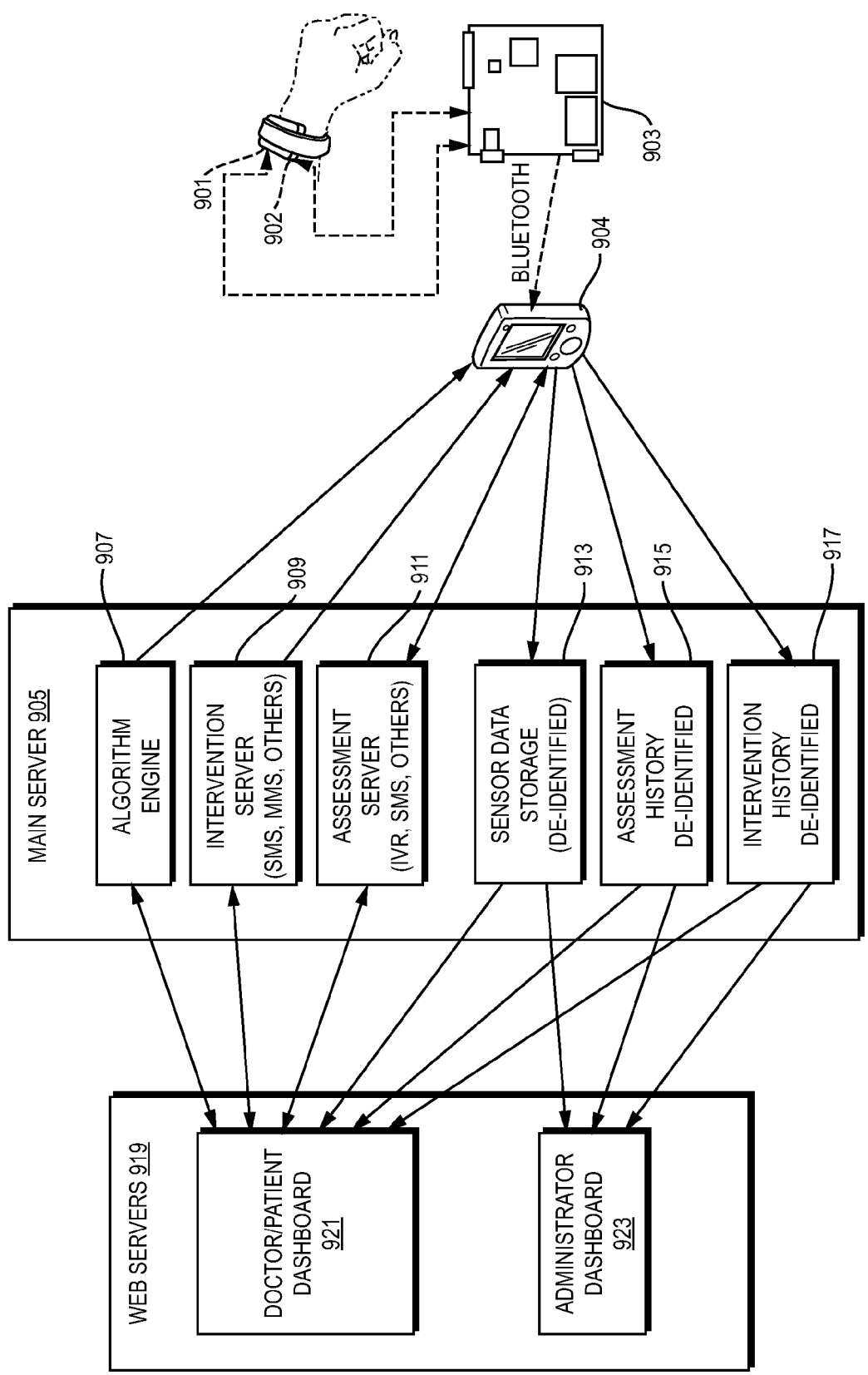
FIG. 20 is a diagram of a different network architecture, in an illustrative implementation of this invention.

Alternately, this invention may be implemented as shown in FIG. 20. The system configuration in FIG. 20 is similar to that in FIG. 19, with a main server 905, algorithm engine 907, intervention server 909, assessment server 911, de-identified sensor data 913, de-identified assessment history 915, de-identified intervention history 917, web servers 919, doctor/patient dashboard 921, and administrator dashboard 923. These function in the manner described for FIG. 19, except as described below. In the example shown in FIG. 20, pattern recognition algorithms may run locally on one or more onboard processors housed in one or more of the following: a mobile phone 904, a data hub 903, or a wearable sensor module 901. The algorithm engine 907 updates these pattern recognition algorithms, and these updated algorithms are sent to these one or more onboard processors, where they run locally. In this example, the hub 903 is not a mobile phone. The hub acts as a "bridge" between the Bluetooth™ enabled mobile phone 904 and an IEEE 802.15.4-enabled sensor 901 and transducer 902. The wearable transducer 902 is used to deliver therapeutic stimuli to a patient.

In some embodiments of this invention, a radio base station or reader is used to collect data from one or more radio modules and sensors. For example, the base station can be the ZR-USB, which has a USB interface to plug into PC's and laptops. This base station may comprise an ATmega168V microcontroller, a CC2420 radio IC, and a FTDI232BQ USB interface chip (Future Technology Devices International, Ltd., Glasgow, United Kingdom). In some implementations, a 50-Ohm antenna port permits a variety of commercially available 2.4 GHz antennas to be used.

This invention may be implemented in such a way that a mobile phone is used as the wireless hub, and the IEEE 802.15.4 wireless protocol is not used. In this approach, Bluetooth™ is used directly to the phone, and then the phone transmits out through the cell phone network to the remote server.

Alternately, this invention may be implemented in such a way that data is sent to a separate wireless hub (e.g., using the IEEE 802.15.4 protocol), and then this hub communicates to the phone. In that case, the patient does not have to wear or carry two different devices (the phone plus the wireless hub). For example, this approach is advantageous where the patient is not very mobile (such as a baby monitor).

In many cases, it is desirable to set an ID code for each sensor radio module and to configure its transmission or sampling rate. In some embodiments, to meet these needs, a command protocol is added using a "command and response" paradigm. Such a command protocol may operate as follows, in an illustrative implementation of this invention. To send a command to a sensor radio module, the command is first sent to another device (such as a cell phone, hub or radio base station). The command is stored in this other device's "command queue" until the sensor radio module wakes up and transmits its data packet to this other device. The command is then transmitted to the sensor radio module, which receives the command and immediately executes it before going back to sleep.

This invention may be implemented in such a way that data from multiple radio modules (e.g. on both left and right wrists) is monitored. In those cases, it may be desirable to synchronize time between sensors. For example, in some embodiments in which the ad-hoc asynchronous nature of the network does not automatically provide a common time base, a radio base station (or other device that receives radio transmissions from sensors) may be programmed to time stamp arriving data packets in order to generate a proper time base of the measurements. Alternately, the sensors themselves may include a real-time clock. Or the devices may auto-synch with a designated node of the networked system In some implementations of this invention, a background process runs on a smartphone or other mobile computing device. This background process automatically collects data from the sensors and relays this data to a central server. For example, the information relayed to the server may be raw data or calculated parameters.

In some embodiments of this invention, self-reports are collected from a patient on a periodic basis (e.g., as a daily assessment). For example, a smartphone may have a chron job that periodically opens a pre-loaded form and prompts the patient to answer some questions. (For instance, the first screen on this form may display "It's time to ask you a few questions. Can we do this now? [YES] [WAIT 5 min] [NO]" If No, then the app will wait half hour or so and try again later.) These forms can be dynamically created and pushed to the phone from the server.

In some embodiments, a server: (a) stores individual profile data for patients, (b) stores content to be used for their interventions (e.g., photos, text messages, audio clips), and (c) keeps track of the interventions they have received. According to principles of this invention, content (such as prerecorded audio or visual content) may be stored in machine-readable form in the memory of a server. This content may be accessed and delivered to a user as therapeutic stimuli in a form perceptible to a user.

In some embodiments, GUIs (a) display an administrator control panel that can be used to enroll new patients or de-activate old ones, and (b) enable a patient and doctor to select or create the content (photos, messages, sounds) to be used for their individual treatment (intervention).

In some embodiments, a software application allows content to be delivered automatically (on a time schedule) to the patients. This content may include following: (a) messages that are sent at regular intervals, and (b) new forms to push to the phone that are used for periodic self-reporting by the patient. For example, these messages may be emails or SMS/MMS messages and these forms may be XForms. Also, for example, some of these messages may provide patients with daily status updates to let them know how they are doing in their therapy. Some messages may simply provide fun activities (e.g. a short game or puzzle) or topics of interest (perhaps news or a tip addressing a patient's hobby or special interest) to the patient, to encourage continued engagement with the system.

In some embodiments, a server analyzes physiological data from the sensors by applying a pattern recognition algorithm to classify the data and identify specific cases. Based on the results of this classification, the server modifies the content and also the parameters of the "content pusher" module (e.g., changes the images or text messages that are sent, changes the frequency that the messages are sent, or changes the "sensitivity" of the algorithm that detects the specific abnormality).

In some implementations of this invention, data is gathered by patients by using IVR (interactive Voice Response).

This invention has numerous applications, in addition to those described above. Here are four examples:

First, this invention may be implemented in such a way that a person who has experienced multiple seizures (epilepsy) wears a sensor on one or both wrists with customized pattern recognition software in a on-board processor that analyzes patterns in autonomic nervous system activation to predict the onset of a seizure. This information can be communicated to a nearby helper, and may also be used to trigger various automatic interventions.

Second, in some embodiments, a person wears a wireless sensor and a processor recognizes the wearer's detectable patterns of physiological change related to threat such as the autonomic nervous system changes that happen in a bank robbery or other high-risk life-threatening situation. The device can be discretely integrated into clothing (wrist watch, shoe, etc.) so that it is not visible. The wireless components allow for multiple individuals (e.g. bank employees) to communicate their state simultaneously, e.g., to somebody who can help intervene on behalf of their safety.

Third, this invention may be implemented for triage in an emergency response to a disaster, such as an earthquake or explosion, with many casualties. In a mass casualty situation, emergency workers generally perform triage, and it is not possible to deploy large and expensive medical equipment to each patient who is injured. The present invention may be implemented so that it is small and portable and can be easily attached to a large number of patients. Data transmitted from each patient to a wireless hub can be analyzed in real time to detect specific states such as hemorrhagic (hypovolemic) shock due to loss of blood, or septic shock due to onset of infection. More specifically, certain physiological signs for the human body inflammatory response have been defined by the American Society of Chest Physicians and Society of Critical Care Medicine (consensus conference 1992) to include the following: (a) body temperature less than 36° C. or greater than 38° C., (b) tachycardia—heart rate greater than 90 bpm, (c) tachypnea—respiration greater than 20 breaths per minute. In this implementation, since the emergency workers are very busy attending to other patients, a machine learning algorithm running on the wireless hub or mobile phone automatically monitors patients wearing the sensors, and automatically detects these dangerous states and triggers a message to be sent to one of the emergency workers.

Fourth, this invention may be implemented to help patients with severe diabetes who are susceptible to diabetic shock (hypoglycemia). In this case, before the patient becomes unconscious, the patient exhibits increased heart rate and high skin conductance (electrodermal activity). In this implementation, the wireless processor "hub" or mobile phone is used to analyze data in real time and initiate a message to a caregiver in the form of an e-mail, SMS text message, or even a phone call.

A few definitions, for clarity:

The term "hub" means an apparatus comprising a plurality of radios, which apparatus is at least capable of receiving radio signals that comply with one wireless protocol and transmitting radio signals that comply with a different wireless protocol. For example, a Bluetooth™-enabled cell phone with a 3G wireless link is a hub.

The term "mobile computing device" means a smartphone, smartbook, notepad computer, subnotepad computer, netbook, tablet computer, internet tablet, personal digital assistant, palmtop computer, laptop computer, mobile phone, cell phone or other portable or handheld computing device.

The term "physiological data" means data relating to a physical state, physical property or physical parameter of a living organism, or a time at which such state, property or parameter occurs. Examples of physiological data include heart rate, breathing rate, skin conductance, biopotentials, core body temperature, and limb movement, and parameters derived from them (e.g., heart rate variability). Physiological data may relate to any living organism, including humans, animals, and also plants (e.g. photosynthesis measurements). Physiological data includes data regarding the physical activity of a living organism. For example, data regarding the position, acceleration or movement of body parts (or GPS data regarding the geographical position or movement of a person) is "physiological data" as defined herein.

The term "sensor" means an electronics module comprising a radio, and one or more sensor elements and circuits for measuring physiological data, such as EDA, heart rate, or temperature. This electronics module may further comprise a data storage module, power supply, and GPS receiver.

The term "therapeutic" means pertaining to the treatment of an adverse medical condition or treatment of unhealthy behavior. "Therapeutic stimuli" may include, for example (a) vibrations or flashes of light, or (b) images, audio files, text messages, and other communications content having psychological impact. "Therapeutic stimuli" may also include stimuli delivered in or as a therapeutic intervention.

The term "verbal" refers to communication that involves, at least in part, words. Verbal communication is not limited to audible communication, but may be perceptible by any other sense, such as visual (e.g. a text or handwritten message) or tactile (e.g., a Braille message).

The term "wireless protocol" means a standard, specification or protocol, in each case for wireless communication. For example, the Bluetooth™ standard and the IEEE 802.15.4 wireless data standard. However, wireless protocol may also include protocols that do not conform to an industry standard, such as a proprietary standard.

CONCLUSION

It is to be understood that the methods and apparatus which have been described above are merely illustrative applications of the principles of the invention. Numerous modifications may be made by those skilled in the art without departing from the scope of the invention. The scope of the invention is not to be limited except by the claims that follow.

What is claimed is:

1. A system comprising, in combination:
(a) at least one wearable biosensor configured (i) for measuring physiological data and (ii) for wirelessly transmitting the data to a hub for direct or indirect transmission to a web server, which server is included in a set of one or more servers;
(b) the one or more servers;
wherein
(i) the at least one biosensor includes a wireless module,
(ii) the one or more servers are configured
(A) to use a pattern recognition algorithm to recognize patterns in the data, and
(B) based on a pattern in the data recognized by the algorithm, to output instructions for one or more transducers to produce psychologically therapeutic stimuli,
(iii) the psychologically therapeutic stimuli comprise auditory, visual or audiovisual stimuli, and (iv) the one or more servers are further configured to perform machine learning to repeatedly update classifiers in a pattern recognition algorithm, which machine learning includes using data from the biosensor for training.

2. The system of claim 1, wherein the hub comprises a mobile computing device.

3. The system of claim 2, wherein the one or more transducers are included in the mobile computing device.

4. The system of claim 1, wherein said pattern is indicative of a drug craving or panic state.

5. The system of claim 1, wherein the psychologically therapeutic stimuli comprise a verbal message.

6. The system of claim 1, wherein the psychologically therapeutic stimuli comprise audio or visual content.

7. The system of claim 1, wherein the psychologically therapeutic stimuli comprise an SMS message or MMS message.

8. The system of claim 1, wherein the one or more transducers are wearable.

9. The system of claim 1, further comprising the one or more transducers.

10. The system of claim 1, wherein the pattern recognition algorithm comprises a Dynamic Bayesian Network.

11. The system of claim 1, wherein the hub is wearable and is configured to store the data, after wireless receiving it and before wirelessly transmitting it.

12. The system of claim 1, wherein said system is adapted to repeatedly:
accept updated physiological data,
use at least some of said updated physiological data as training data for machine learning,
based on said machine learning, revise at least one pattern recognition algorithm, and
use said revised pattern recognition algorithm in a processor housed onboard a wearable or handheld device.

13. The system of claim 1, wherein the one or more servers are further adapted for analyzing said physiological data regarding a user, accessing audio or visual content stored in machine-readable form in memory, and outputting instructions for at least one said transducer to deliver said content to said user in a form perceptible to said user.

14. The system of claim 1, wherein said system is adapted for performing said pattern recognition in real time.

15. The system of claim 1, wherein said system is further adapted for soliciting at least one live human communication and outputting instructions for said communication to be delivered to a person wearing said at least one sensor.

16. A method comprising, in combination:
(a) using a biosensor to measure physiologic data regarding a human;
(b) wirelessly transmitting the data to a mobile computing device; and
(c) using one or more processors:
(i) to recognize a pattern in the data using a pattern recognition algorithm,
(ii) to output instructions for one or more transducers to produce psychologically therapeutic stimuli, and
wherein
(1) the psychologically therapeutic stimuli comprise auditory, visual or audiovisual stimuli, and
(2) the one or more processors are configured to dynamically modify the pattern recognition algorithm with updated classifiers.

17. The method of claim 16, wherein the one or more processors that recognize a pattern (step 16(c)(i)) are onboard the mobile computing device.

18. The method of claim 16, wherein the one or more processors that recognize a pattern (step 16(c)(i)) and output instructions (step 16(c)(ii)) are onboard the mobile computing device.

19. The method of claim 16, wherein all or some of the transducers are onboard the mobile computing device.

20. The method of claim 18, wherein the method includes receiving the updated classifiers directly or indirectly from another computer, but the method does not include computing the updated classifiers.

\* \* \* \* \*